(12) United States Patent
Moschel et al.

(10) Patent No.: US 7,825,096 B2
(45) Date of Patent: Nov. 2, 2010

(54) O6-ALKYLGUANINE-DNA ALKYLTRANSFERASE INACTIVATORS AND BETA-GLUCURONIDASE CLEAVABLE PRODRUGS

(75) Inventors: Robert C. Moschel, Frederick, MD (US); Matthew Karl Moschel, legal representative, Baltimore, MD (US); Natalia A. Loktionova, Hershey, PA (US); Anthony E. Pegg, Hershey, PA (US); Gary T. Pauly, Frederick, MD (US)

(73) Assignees: The United States of America as represented by the Department of Health and Human Services, Washington, DC (US); The Penn State Research Foundation, University Park, PA (US)

(*) Notice: Subject to any disclaimer, the term of this patent is extended or adjusted under 35 U.S.C. 154(b) by 747 days.

(21) Appl. No.: 11/683,310

(22) Filed: Mar. 7, 2007

(65) Prior Publication Data
US 2007/0213279 A1 Sep. 13, 2007

Related U.S. Application Data

(63) Continuation-in-part of application No. PCT/US2005/031506, filed on Sep. 6, 2005.

(60) Provisional application No. 60/608,045, filed on Sep. 8, 2004.

(51) Int. Cl.
*A01N 43/04* (2006.01)
*A61K 31/70* (2006.01)

(52) U.S. Cl. .............................. 514/43; 514/42; 514/45; 514/46

(58) Field of Classification Search .................. None
See application file for complete search history.

(56) References Cited

U.S. PATENT DOCUMENTS

| | | | |
|---|---|---|---|
| 4,235,871 A | 11/1980 | Papahadjopoulos et al. |
| 4,501,728 A | 2/1985 | Geho et al. |
| 4,837,028 A | 6/1989 | Allen |
| 5,019,369 A | 5/1991 | Presant et al. |
| 5,091,430 A | 2/1992 | Moschel et al. |
| 5,352,669 A | 10/1994 | Moschel et al. |
| 5,358,952 A | 10/1994 | Moschel et al. |
| 5,525,606 A | 6/1996 | Moschel et al. |
| 5,561,119 A | 10/1996 | Jacquesy et al. |
| 5,691,307 A | 11/1997 | Moschel et al. |
| 5,753,668 A | 5/1998 | Moschel et al. |
| 5,916,894 A | 6/1999 | Moschel et al. |
| 5,929,046 A | 7/1999 | McMurry et al. |
| 5,935,995 A | 8/1999 | Bosslet et al. |
| 5,955,100 A | 9/1999 | Bosslet et al. |
| 5,958,932 A | 9/1999 | Moschel et al. |
| 6,060,458 A | 5/2000 | Moschel et al. |
| 6,096,724 A | 8/2000 | McMurry et al. |
| 6,172,070 B1 | 1/2001 | Moschel et al. |
| 6,303,604 B1 | 10/2001 | Moschel et al. |
| 6,333,331 B1 | 12/2001 | Moschel et al. |
| 6,436,945 B2 | 8/2002 | Moschel et al. |

FOREIGN PATENT DOCUMENTS

| | | |
|---|---|---|
| CN | 1861078 A | 11/2006 |
| EP | 1142893 | 10/2001 |
| JP | 07267955 A | 10/1995 |
| JP | 07267956 A | 10/1995 |
| WO | WO 96/04281 A | 2/1996 |
| WO | WO 97/20843 A1 | 6/1997 |
| WO | WO 02/083937 A2 | 10/2002 |
| WO | WO 2004/031404 A1 | 4/2004 |
| WO | WO 2004/031405 A1 | 4/2004 |
| WO | WO 2005/085431 A2 | 9/2005 |
| WO | WO 2005/085470 A1 | 9/2005 |
| WO | WO 2006/029065 A | 3/2006 |

OTHER PUBLICATIONS

KEppler et al. Methods (2004), vol. 32, pp. 437-444.*
Bagshawe et al., "A cytotoxic agent can be generated selectively at cancer sites," *Br. J. Cancer*, 58, 700-703 (1988).
Bosslet et al., "Elucidation of the mechanism enabling tumor selective prodrug monotherapy[1]," *Cancer Res.*, 58, 1195-1201 (1998).
Bosslet et al., "A novel one-step tumor-selective prodrug activation system," *Tumor Targeting*, 1, 45-50 (1995).

(Continued)

*Primary Examiner*—Patrick T Lewis
(74) *Attorney, Agent, or Firm*—Leydig, Voit & Mayer, Ltd.

(57) ABSTRACT

Disclosed are prodrugs of inactivators of $O^6$-alkylguanine-DNA alkyltransferase (AGT). The prodrugs are cleavable by the β-glucuronidase enzyme, which is either administered to the patient or produced by necrotic tumor cells. The prodrugs are represented by the formula A-B-C, wherein A is a glucuronosyl residue linked through its 1-oxygen to the phenyl ring of B; B is a benzyloxycarbonyl group, optionally ring-substituted with one or more electron withdrawing groups; and C is an inactivator of AGT, e.g., a substituted or unsubstituted $O^6$-benzylguanine or $O^6$-benzyl-2'-deoxyguanosine. Also disclosed are additional inactivators of AGT, pharmaceutical compositions comprising an inactivator or prodrug and a pharmaceutically acceptable carrier, and a method of use of the inactivator or prodrug in enhancing the chemotherapeutic treatment of tumor cells in a mammal, e.g., a human, with an antineoplastic alkylating agent that causes cytotoxic lesions at the $O^6$-position of guanine.

6 Claims, 5 Drawing Sheets

OTHER PUBLICATIONS

Carl et al., "A novel connector linkage applicable in prodrug design," *J. Med. Chem.*, 24, 479-480(1981).

Covalys Biosciences AG, "BG-NH$_2$ building block for SNAP-tag substrates," 1-4 (2006).

Damoiseaux et al., "Synthesis and Applications of Chemical Probes for Human O6-Alkylguanine-DNA Alkyltransferase," *ChemBioChem.*, 4, 285-287 (2001).

Damoiseaux et al., "Towards the Generation of Artificial O$^6$-Alkylguanine-DNA Alkyltransferases: In Vitro Selection of Antibodies with Reactive Cysteine Residues," *ChemBioChem.*, 6, 573-575 (2002).

De Graaf et al., "Beta-glucuronidase-mediated drug release," *Curr. Pharm. Design*, 8, 1391-1403(2002).

De Groot et al., "Anticancer Prodrugs for Application in Monotherapy: Targeting Hypoxia, Tumor-Associated Enzymes, and Receptors," *Curr. Med. Chem.*, 8, 1093-1122 (2001).

Dolan et al., "Effect of O$^6$-benzylguanine on the sensitivity of human colon tumor xenograftsto 1,3-bis(2-chloroethyl)-1-nitrosourea (BCNU)," *Biochem. Pharmacol.*, 46, 285-290 (1993).

Felker et al., "Treatment of subcutaneous and intracranial brain tumor xenografts with O$^6$-benzylguanine and 1,3-bis(2-chloroethyi)-1-nitrosourea," *Cancer Chemo. Pharmacol.*, 32, 471-476 (1993).

Florent et al., "Prodrugs of anthracyclines for use in antibody-directed enzyme prodrug therapy," *J. Med. Chem.*, 41, 3572-3581 (1998).

Haisma et al., "A monoclonal antibody-β-glucuronidase conjugate as activator of the prodrug epirubicin-glucuronide for specific treatment of cancer," *Br. J. Cancer*, 66, 474-478 (1992).

Houba et al., "Characterization of novel anthracycline prodrugs activated by human β-glucuronidase for use in antibody-directed enzyme prodrug therapy," *Biochem. Pharmacol.*, 52, 455-463 (1996).

Houba et al., "A novel doxorubicin-glucuronide prodrug DOX-GA3 for tumour-selective chemotherapy: distribution and efficacy in experimental human ovarian cancer," *Br. J. Cancer*, 84, 550-557 (2001).

Juillerat et al., "Directed Evolution of O6-Alkylguanine-DNA Alkyltransferase for Efficient Labeling of Fusion Proteins with Small Molecules In Vivo," *Chemistry & Biology*, 10, 313-317 (2003).

Keppler et al., "A general method for the covalent labeling of fusion proteins with small molecules in vivo," *Nature Biotechnology*, 21, 86-89 (2003).

Keppler et al., "Labeling of fusion proteins with synthetic fluorophores in live cells," *PNAS*, 101, 9955-9959 (2004).

Keppler et al., "Labeling of fusion proteins of O$^6$-alkylguanine-DNA alkyltransferase with small molecules in vivo and in vitro," *Methods*, 32, 437-444 (2004).

Kindermann et al., "Covalent and Selective Immobilization of Fusion Proteins," *J. Am. Chem. Soc.*, 125, 7810-7811 (2003).

Kokkinakis et al., "Eradication of human medulloblastema tumor xenografts with a combination of O$^6$-benzyl-2'-deoxyguanosine and 1,3-bis(2-chloroethyl)1-nitrosourea," *Clin. Cancer Res.*, 5, 3676-3681 (1999).

Kurpad et al., "Intraarterial O$^6$-benzylguanine enables the specific therapy of nitrosourea-resistant intracranial human glioma xenografts in athymic rats with 1,3-bis(2-chloroethyl)-1-nitrosourea," *Cancer Chemo. Pharmacol.*, 39, 307-316 (1997).

Leenders et al., "Novel anthracycline-spacer-β-glucuronide,-β-glucoside, and-β-galactoside prodrugs for application in selective chemotherapy," *Bioorg. Med. Chem.*, 7, 1597-1610 (1999).

Leu et al., "Design and synthesis of water-soluble glucuronide derivatives of camptothecin for cancer prodrug monotherapy and antibody-directed enzyme prodrug therapy (ADEPT)," *J. Med. Chem.*, 42, 3623-3628 (1999).

Longo, "The use of chemotherapy in the treatment of Hodgkin's disease," *Semin. Concol.*, 17, 716-735 (1990).

Lougerstay-Madec et al., "Synthesis of self-immolative glucuronide-based prodrugs of a phenol mustard," *Anti-Cancer Drug Des.*, 13, 995-1007 (1998).

Madec-Lougerstay et al., "Synthesis of self-immolative glucuronide spacers based on aminomethylcarbamate. Application to 5-fluorouracil prodrugs for antibody-directed enzyme prodrug therapy," *J. Chem. Soc., Perkin Trans.*, 1, 1369-1375 (1999).

McCormick et al., "Nitrosoureas from chemist to physician: classification and recent approaches to drug design," *Eur. J. Cancer*, 26, 207-221 (1990).

Pegg et al., "Structure, function, and inhibition of O$^6$-alkylguanine-DNA alkyltransferase," *Prog. Nucleic Acid Res. Mol. Biol.*, 51, 167-223 (1995).

Pegg, "Mammalian O$^6$-alkylguanine-DNA alkyltransferase: regulation and importance in response to alkylating carcinogenic and therapeutic agents," *Cancer Research*, 50, 6119-6129 (1990).

Quinn et al., "Phase II trial of carmustine plus O$^6$-benzylguanine for patients with nitrosourea-resistant recurrent or progressive malignant glioma," *J. Clin. Oncol.*, 20, 2277-2283 (2002).

Schaller et al., "Studies on Polynucleotides. XXIV.[1] The Stepwise Synthesis of Specific Deoxyribopolynucleotides (4).[2] Protected Derivatives of Deoxyribonucleosides and New Syntheses of Deoxyribonucleoside-3' Phosphates[3]," *J. Amer. Chem. Soc.*, 85, 3821-3827 (1963).

Schmidt et al., "Prodrug Mono Therapy: synthesis and biological evaluation of an etoposide glucuronide-prodrug," *Bioorg. Med. Chem.*, 11, 2277-2283 (2003).

Schmidt et al., "Glucuronide Prodrugs of Hydroxy Compounds for Antibody Directed Enzyme Prodrug Therapy (ADEPT): A Phenol Nitrogen Mustard Carbamate," *Bioorg. Med. Chem. Lett.*, 7, 1071-1076 (1997).

Schold, Jr. et al., "Treatment of human brain tumor xenografts with O$^6$-benzyl-2'-deoxyguanosine and BCNU[1]," *Cancer Res.*, 56, 2076-2081 (1996).

Szoka et al., "Comparative properties and methods of preparation of lipid vesicles (liposomes)[1]," *Ann. Rev. Biophys. Bioeng.*, 9, 467-508 (1980).

Wasserman et al., "Clinical comparison of the nitrosoureas," *Cancer*, 36, 1258-1268 (1975).

Wei et al., "Beta-glucuronidase-cleavable prodrugs of O$^6$-benzylguanine and O$^6$-benzyl-2'-deoxyguanosine," *Journal of Medicinal Chemistry*, 48 (2004).

Zajc et al., "Epoxide and Diol Epoxide Adducts of Polycyclic Aromatic Hydrocarbons at the Exocyclic Amino Group of Deoxyguanosine," *Tet. Lett*, 33, 3409-3412 (1992).

* cited by examiner

O6-ALKYLGUANINE-DNA ALKYLTRANSFERASE INACTIVATORS AND BETA-GLUCURONIDASE CLEAVABLE PRODRUGS

CROSS-REFERENCE TO RELATED APPLICATIONS

This is a continuation-in-part of PCT/US2005/031506, filed Sep. 6, 2005, which claims the benefit of U.S. Provisional Patent Application No. 60/608,045, filed Sep. 8, 2004; the disclosure of these applications is incorporated by reference.

STATEMENT REGARDING FEDERALLY SPONSORED RESEARCH AND DEVELOPMENT

This invention was made with Government support under Grant No. CA071976, awarded by the National Institutes of Health. The Government has certain rights in the invention.

FIELD OF THE INVENTION

The present invention relates to inactivators of $O^6$-alkylguanine-DNA alkyltransferase (AGT) and prodrugs of such inactivators. The prodrugs are cleaved by the beta-glucuronidase enzyme found in tumor cells or co-administered to the patient, and are targeted for use in cancer treatment in combination with an antineoplastic alkylating agent such as 1,3-bis(2-chloroethyl)-1-nitrosourea (BCNU) or temozolomide.

BACKGROUND OF THE INVENTION

AGT is a DNA repair protein. AGT removes alkyl and aralkyl groups that become attached at the $O^6$-position of guanine in DNA following exposure to mutagenic and/or carcinogenic alkylating agents. It does so by bringing about a stoichiometric transfer of the group attached to the $O^6$-position of a guanine residue in DNA to a cysteine residue within the AGT protein. Pegg, *Cancer Research* 50: 6119-6129 (1990). Accordingly, AGT is beneficial to a normal cell because it removes the adducts that are formed in DNA by toxic, mutagenic and carcinogenic agents, thereby restoring the DNA to its original state and helping to prevent DNA mutations that can lead to initiation of tumor formation. Unfortunately, AGT is also beneficial to a cancerous cell because it also removes those adducts that are formed at the $O^6$-position of guanine in DNA by antineoplastic alkylating agents, such as monofunctional methylating agents, e.g., procarbazine, dacarbazine and temozolomide, and chloroethylating agents, i.e., cbloroethylnitrosoureas (CENUs), such as BCNU, ACNU, CCNU, and MeCCNU. Pegg et al., *Prog. Nucleic Acid Research Molec. Biol.* 51: 167-223 (1995). The resulting alkylated AGT molecule is consequently inactivated and is unable to carry out subsequent dealkylation reactions. The presence of more AGT in a cell increases its capacity to repair DNA by this mechanism compared to a cell that has less AGT.

The reduction in the efficacy of cancer chemotherapeutic drugs due to AGT, which acts without requiring the presence of additional enzymes or cofactors, and the existence of a high correlation between AGT activity and reduction in sensitivity of tumor cells to nitrosoureas have led to AGT becoming a prime target for modulation. Modulation has been attempted by two different routes. One route is indirect and involves the use of methylating agents that introduce $O^6$-methylguanine lesions into DNA for subsequent repair by AGT, thereby depleting levels of AGT. The other route is direct and involves the use of an adjuvant, i.e., an inactivator of AGT, such as an $O^6$-aralkylguanine, e.g., $O^6$-benzylguanine; see, for example, Moschel et al., U.S. Pat. Nos. 5,091,430; 5,352,669; 5,358,952; 5,525,606; 5,691,307; 5,753,668; 5,916,894; 5,958,932; 6,060,458; 6,172,070; 6,303,604; 6,333,331; and 6,436,945. It has been shown that such adjuvants can inactivate AGT and that this inactivation can markedly improve the effectiveness of chemotherapeutic drugs that modify the $O^6$-position of DNA guanine residues. Pegg et al., *Prog. Nucleic Acid Res. Mol. Biol.* 51: 167-223 (1995); Kokkinakis et al., *Clin. Cancer Res.* 5: 3676-3681 (1999); Dolan et al., *Biochem. Pharmacol.* 46: 285-290 (1993); Felker et al., *Cancer Chemo. Pharmacol.* 32: 471-476 (1993); Schold, Jr. et al., *Cancer Res.* 56: 2076-2081 (1996); and Kurpad et al., *Cancer Chemo. Pharmacol* 39: 307-316 (1997). In some instances, however, in clinical trials, the adjuvant therapy produces toxic side effects in the patient. Quinn et al., *J. Clin. Oncol.* 2002, 20, 2277-2283.

There is a desire, therefore, to minimize the toxic side effects of the adjuvant therapy. The foregoing shows that there exists a need for adjuvants that are selective to the tumor cell. The present invention provides such an approach. The advantages of the present invention as well as inventive features will be apparent from the description of the invention provided below.

SUMMARY OF THE INVENTION

Figure 1A:
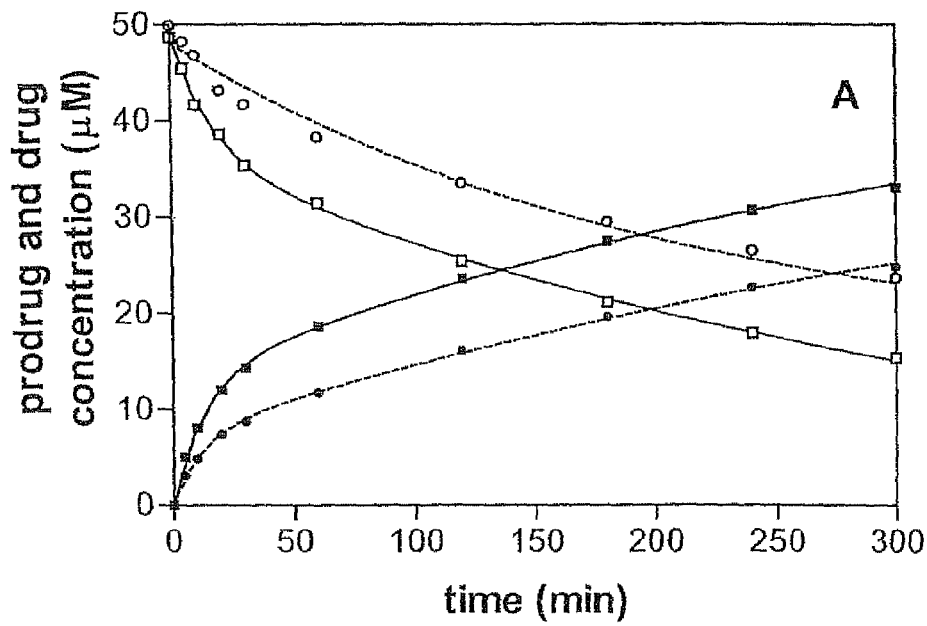
FIG. 1A depicts the concentration of prodrugs 1 (open squares) and 2 (open circles); and of $O^6$-benzylguanine (closed squares) and $O^6$-benzyl-2'-deoxyguanosine (closed circles), which were produced by the enzymatic cleavage of the prodrugs, as a function of time in contact with 10-units/mL bovine liver β-glucuronidase.

The present invention provides for ameliorating a disadvantage of some of the known $O^6$-alkylguanine-DNA alkyltransferase inactivators. The present invention provides prodrugs of AGT inactivators. The prodrug includes a glycosyl residue, e.g., glucuronosyl, which is cleavable by the β-glucuronidase enzyme, and which is either administered and/or found on tumor cells. The cleavage by the enzyme releases the inactivator in the vicinity of the tumor cells. As a result, the inactivator is more selective for tumor cells and toxicity to the patient is therefore minimized.

The present invention further provides a pharmaceutical composition comprising a prodrug of the invention and a pharmaceutically acceptable carrier. The present invention further provides a method of enhancing the chemotherapeutic treatment of tumor cells in a mammal with an antineoplastic alkylating agent that causes cytotoxic lesions at the $O^6$-position of guanine. The method comprises administering to the mammal an effective amount of a prodrug and antineoplastic alkylating agent, and optionally the β-glucuronidase enzyme. The present invention also provides a method of inactivating AGT in a tumor cell comprising contacting said tumor cell with an effective amount of a compound or prodrug of the invention and an effective amount of a β-glucuronidase enzyme.

The invention also provides inactivators of the AGT, pharmaceutical compositions comprising such inactivators, and method of use thereof.

While the invention has been described and disclosed below in connection with certain embodiments and procedures, it is not intended to limit the invention to those specific embodiments. Rather it is intended to cover all such alternative embodiments and modifications as fall within the spirit and scope of the invention.

DETAILED DESCRIPTION OF THE INVENTION

The present invention is predicated on the concept that enzymatic conversion of a prodrug to an active drug in the vicinity of a tumor cell provides an approach for delivering an inactivator of AGT more selectively to tumor cells versus normal cells of a host. This approach relies on activation by enzymes that are expressed or released by tumor cells. β-Glucuronidase is an example of a lysosomal hydrolase that is released from necrotic tumor cells found within poorly vascularized regions of tumor masses (Bosslet et al., Tumor Targeting 1995, 1, 45-50; Cancer Res. 1998, 58, 1195-1201; and de Graaf et al., Curr. Pharm. Design 2002, 8, 1391-1403). When the prodrug is cleaved by β-glucuronidase, the released active drug enters nearby tumor cells preferentially, thereby minimizing the more widespread toxicity associated with systemic delivery of some of the unmodified drugs.

In accordance with an embodiment, the present invention provides a compound (or prodrug) of the formula: A-B-C, wherein A is a glucuronosyl residue linked through its 1-oxygen to the phenyl ring of B; B is a benzyloxycarbonyl group, optionally ring-substituted with one or more electron withdrawing groups; and C is an inactivator of $O^6$-alkylguanine-DNA alkyltransferase (AGT) linked to the carbonyl of B, or a pharmaceutically acceptable salt thereof.

The glucuronosyl residue (A) can be any suitable enzymatically cleavable poly-oligo, or monosaccharide, For example, the glucuronosyl residue is a D-glucuronosyl residue. The hydroxyl groups of the glucuronosyl residue may be free or protected, e.g., by an ester group that is removed enzymatically or hydrolyzed spontaneously, such as an acetyl or mono-, di-, or trihaloacetyl protective group, with the halogen being fluorine or chlorine, or benzyl protective group. The protective group may be released to provide a substrate for the β-glucuronidase enzyme. The acid group of the prodrug may be converted to a salt such as a sodium salt. It has been shown that prodrugs of certain drugs, e.g., anthracyclines and nitrogen mustards, which contain a glucuronic acid residue linked through a self-immolating linker are cleavable by the β-glucuronidase enzyme. Leenders et al., Bioorg. Med. Chem. 1999, 7, 1597-1610; Houba et al., Br. J. Cancer 2001, 84, 550-557; Schmidt et al., Bioorg. Med. Chem. Lett. 1997, 7, 1071-1076; Lougerstay-Madec et al., Anti-Cancer Drug Des. 1998, 13, 995-1007; Florent et al., J. Med Chem. 1998, 41, 3572-3581; Lougerstay-Madec et al., J. Chem. Soc.—Perkin Trans. 1 1999, 1369-1375; Leu et al., J. Med. Chem. 1999, 42, 3623-3628; and Schmidt et al., Bioorg. Med. Chem. 2003, 11, 2277-2283.

The electron withdrawing group can be present on the phenyl ring of B at any suitable position, for example, the meta, or preferably ortho, position relative to the oxygen linking B to the glucuronosyl residue. Any suitable electron-withdrawing group (B) can be employed. Examples of electron withdrawing groups include nitro, halo, alkylsulfonyl, cyano, trifluoroalkoxy, trifluoroalkylthio, alkylcarbonyloxy, nitroso, formyl, alkoxycarbonyl, alkylcarbonyl, thiol, sulfamoyl, alkylsulfamoyl, chloroalkyl, ammonium, hydroxyalkyl, phenyl, N,N-dialkylamino and its ammonium salt, and vinyl.

For example, the electron withdrawing group may be selected from the group consisting of nitro, halo, $C_1$-$C_6$ alkylsulfonyl, cyano, trifluoro $C_1$-$C_6$ alkoxy, trifluoro $C_1$-$C_6$ alkylthio, $C_1$-$C_6$ alkylcarbonyloxy, nitroso, formyl, $C_1$-$C_6$ alkoxycarbonyl, $C_1$-$C_6$ alkylcarbonyl, hydroxy, thiol, sulfamoyl, $C_1$-$C_6$ alkylsulfamoyl, chloro $C_1$-$C_6$ alkyl, amino, hydroxy $C_1$-$C_6$ alkyl, phenyl, N,N-$C_1$-$C_6$ dialkylamino, and vinyl, and preferably selected from the group consisting of nitro, halo, methylsulfonyl, cyano, trifluoromethoxy, trifluoromethylthio, acyloxy, nitroso, formyl, methoxycarbonyl, acetyl, thiol, sulfamoyl, methylsulfamoyl, chloromethyl, ammonium, hydroxymethyl, phenyl, N,N-dimethylamino and it ammonium salt, and vinyl. The halo group can be fluoro, chloro, bromo, or iodo. A preferred electron-withdrawing group is nitro. A nitrobenzylphenoxycarbamate linker (Carl et al., J. Med. Chem. 1981, 24, 479-480) has been shown for doxorubicin prodrugs (Florent et al., J. Med. Chem. 1998, 41, 3572-3581) and 5-fluoruracil prodrugs (Laugerstay-Madec et al., J. Chem. Soc.—Perkin Trans. 1 1999, 1369-1375) to self-immolate efficiently once the respective glucuronides are cleaved.

Any suitable inactivator of AGT can be employed in accordance with the present invention. Examples of inactivators of AGT include unsubstituted or substituted $O^6$-benzylguanine (see formula below), $O^6$-benzyl-8-azaguanine, $O^6$-benzyloxy pyrimidine, and 2,4-diamino-$O^6$-benzyloxy-s-triazine, preferably an unsubstituted or substituted $O^6$-benzylguanine or an unsubstituted or substituted $O^6$-benzyl-2'-deoxyguanosine. The inactivator of AGT is preferably linked through the $N^2$-position to the carbonyl of B.

The benzyl group of the substituted $O^6$-benzylguanine, substituted $O^6$-benzyl-2'-deoxyguanosine, substituted $O^6$-benzyloxy pyrimidine, substituted $O^6$-benzyl-8-azaguanine, and substituted 2,4-diamino-$O^6$-benzyloxy-s-triazine may have one or more substituents (R group), in place of hydrogen, selected from the group consisting of halogen, hydroxy, aryl, a $C_1$-$C_8$ alkyl substituted aryl, nitro, a polycyclic aromatic alkyl containing 2-4 aromatic rings wherein the alkyl is a $C_1$-$C_6$, a $C_3$-$C_8$ cycloalkyl, a $C_2$-$C_6$ alkenyl, a $C_2$-$C_6$ alkynyl, a $C_1$-$C_6$ hydroxyalkyl, a $C_1$-$C_8$ alkoxy, a $C_2$-$C_8$ alkoxyalkyl, aryloxy, acyloxy, an acyloxyalkyl wherein the alkyl is $C_1$-$C_6$, amino, a monoalkylamino wherein the alkyl is $C_1$-$C_6$, a dialkylamino wherein the alkyl is $C_1$-$C_6$, acylamino, ureido, thioureido, carboxy, a carboxyalkyl wherein the alkyl is $C_1$-$C_6$, cyano, a cyanoalkyl wherein the alkyl is $C_1$-$C_6$, C-formyl, C-acyl, a dialkoxymethyl wherein the alkoxy is $C_1$-$C_6$, an aminoalkyl wherein the alkyl is $C_1$-$C_6$, and $SOn R_1$ wherein n=0, 1, 2 or 3, $R_1$ is H, a $C_1$-$C_6$ alkyl, or aryl. The term "aryl" stands for an aromatic ring of 6-14 carbon atoms, e.g., phenyl, naphthyl, biphenyl, anthracenyl, and the like.

In a specific embodiment, the invention provides a substituted $O^6$-benzylguanine, wherein the benzyl group has an aminoalkyl substituent, which can be present on the ortho, para, or meta position, particularly the para or meta position.

In accordance with an embodiment, the $O^6$-benzylguanine or substituted $O^6$-benzylguanine may also include a substituent at the 8- and/or 9-position; the R group in the formula below represents a substituent on the phenyl ring.

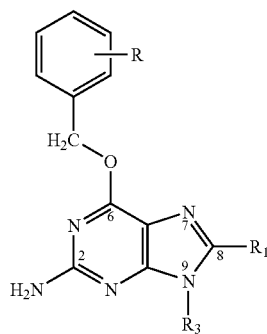

(I)

The 8-position substituent ($R_1$) may be selected from the group consisting of hydrogen, halo, $C_1$-$C_4$ alkyl, $C_1$-$C_4$ hydroxyalkyl, thiol, $C_1$-$C_4$ alkylthio, trifluoromethylthio, $C_1$-$C_4$ thioacyl, hydroxy, $C_1$-$C_4$ alkoxy, trifluoromethoxy, methanesulfonyloxy, trifluoromethanesulfonyloxy, $C_1$-$C_4$ acyloxy, amino, $C_1$-$C_4$ aminoalkyl, $C_1$-$C_4$ alkylamino, $C_1$-$C_4$ dialkylamino, trifluoromethylamino, ditrifluoromethylamino, aminomethanesulfonyl, $C_1$-$C_4$ aminoacyl, aminotrifluoromethylcarbonyl, formylamino, nitro, nitroso, $C_1$-$C_4$ alkyldiazo, $C_5$-$C_6$ aryldiazo, trifluoromethyl, $C_1$-$C_4$ haloalkyl, halomethyl, $C_1$-$C_4$ cyanoalkyl, cyanomethyl, cyano, $C_1$-$C_4$ alkyloxycarbonyl, $C_1$-$C_4$ alkylcarbonyl, phenyl, phenylcarbonyl, formyl, $C_1$-$C_4$ alkoxymethyl, phenoxymethyl, $C_2$-$C_4$ vinyl, $C_2$-$C_4$ ethynyl, and $SO_nR'$ wherein n is 0, 1, 2, or 3 and R' is hydrogen, $C_1$-$C_4$ alkyl, amino, or phenyl; and the 9-position substituent ($R_3$) may be selected from the group consisting of hydrogen, $C_1$-$C_4$ alkyl, $C_1$-$C_4$ aminoalkyl, $C_1$-$C_4$ hydroxyalkyl, $C_1$-$C_4$ alkylaminoalkyl, $C_1$-$C_4$ dialkylaminoalkyl, $C_1$-$C_4$ cyanoalkyl, $C_1$-$C_4$ carbamoylalkyl, $C_1$-$C_4$ pivaloylalkyl, $C_1$-$C_6$ alkylcarbonyloxy $C_1$-$C_4$ alkyl, $C_1$-$C_4$ alkoxycarbonylalkyl, ribose, 2'-deoxyribose, the conjugate acid form of a $C_1$-$C_4$ carboxyalkyl, and the carboxylate anion of a $C_1$-$C_4$ carboxyalkyl as the sodium salt Tautomers may also be used, e.g., the substituent at the 8-position may be an oxo group instead of a hydroxy group.

According to another embodiment, the inactivator of AGT may be an unsubstituted or substituted $O^6$-benzyl-8-azaguanine, preferably linked through the $N^2$-position to the carbonyl of B.

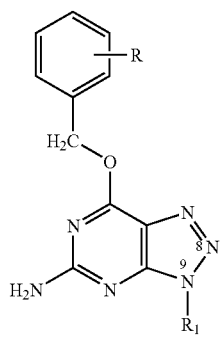

(II)

The $O^6$-benzyl-8-azaguanine may also include a substituent $R_1$ at the 9-position selected from the group consisting of $C_1$-$C_4$ alkyl, $C_1$-$C_4$ alkyloxycarbonyl $C_1$-$C_4$ alkyl, carboxy $C_1$-$C_4$ alkyl, cyano $C_1$-$C_4$ alkyl, aminocarbonyl $C_1$-$C_4$ alkyl, hydroxy $C_1$-$C_4$ alkyl, and $C_1$-$C_4$ alkyloxy $C_1$-$C_4$ alkyl.

In another embodiment, the inactivator of AGT may be an unsubstituted or substituted $O^6$-benzyloxy pyrimidine, preferably linked through the $N^2$-position to the carbonyl of B. The $O^6$-benzyloxy pyrimidine may also include a substituent at its 4- and/or 5-position.

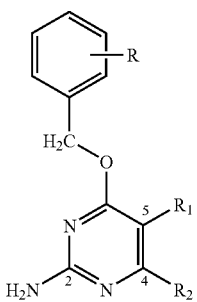

(III)

For example, the 4-position substituent ($R_2$) may be selected from the group consisting of hydrogen, halo, amino, $C_1$-$C_4$ alkyl, $C_1$-$C_4$ hydroxyalkyl, thiol, $C_1$-$C_4$ alkylthio, trifluoromethylthio, $C_1$-$C_4$ thioacyl, hydroxy, $C_1$-$C_4$ alkyloxy, trifluoromethoxy, methanesulfonyloxy, trifluoromethanesulfonyloxy, $C_1$-$C_4$ acyloxy, $C_1$-$C_4$ aminoalkyl, $C_1$-$C_4$ alkylamino, $C_1$-$C_4$ dialkylamino, trifluoromethylamino, ditrifluoromethylamino, aminomethanesulfonyl, amino $C_1$-$C_4$ alkylcarbonyl, aminotrifluoromethylcarbonyl, formylamino, nitro, nitroso, $C_1$-$C_4$ alkyldiazo, $C_5$-$C_6$ aryldiazo, trifluoromethyl, $C_1$-$C_4$ haloalkyl, cyanomethyl, $C_1$-$C_4$ cyanoalkyl, cyano, $C_1$-$C_4$ alkyloxycarbonyl, $C_1$-$C_4$ alkylcarbonyl, phenyl, phenylcarbonyl, formyl, $C_1$-$C_4$ alkoxymethyl, phenoxymethyl, $C_2$-$C_4$ vinyl, $C_2$-$C_4$ ethynyl, and $SO_nR'$ wherein n is 0, 1, 2, or 3 and R' is hydrogen, $C_1$-$C_4$ alkyl, amino, or phenyl; and the 5-position substituent ($R_1$) may be $NO_2$ or NO.

A preferred example of the prodrug of the present invention is:

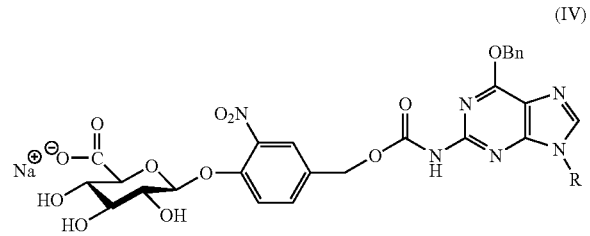

wherein R is H or

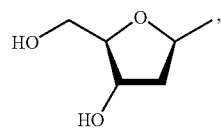

wherein Bn stands for benzyl, which may be optionally substituted as discussed above.

The prodrugs or inactivators may be used as pharmaceutically acceptable salts. Examples of pharmaceutically acceptable salts include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, and arylsulfonic acids. An example of arylsulphonic acid is p-toluenesulphonic acid. The carboxyl group of the prodrug may be converted to salts known to those skilled in the art, for example, a salt of an alkali metal (e.g., sodium or potassium), alkaline earth metal (e.g., calcium), or ammonium salt.

In another embodiment, the invention provides a compound of the formula (I):

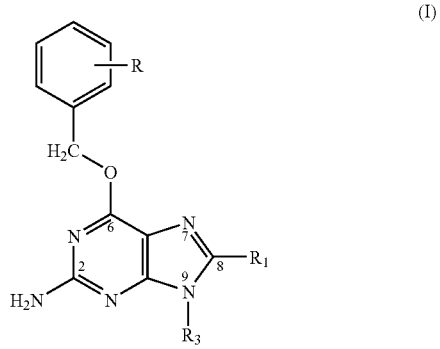

wherein R is amino $C_1$-$C_6$ alkyl;

$R_1$ is selected from the group consisting of hydrogen, halo, $C_1$-$C_4$ alkyl, $C_1$-$C_4$ hydroxyalkyl, thiol, $C_1$-$C_4$ alkylthio, trifluoromethylthio, $C_1$-$C_4$ thioacyl, hydroxy, $C_1$-$C_4$ alkoxy, trifluoromethoxy, methanesulfonyloxy, trifluoromethanesulfonyloxy, $C_1$-$C_4$ acyloxy, amino, $C_1$-$C_4$ aminoalkyl, $C_1$-$C_4$ alkylamino, $C_1$-$C_4$ dialkylamino, trifluoromethylamino, ditrifluoromethylamino, aminomethanesulfonyl, $C_1$-$C_4$ aminoacyl, aminotrifluoromethylcarbonyl, formylamino, nitro, nitroso, $C_1$-$C_4$ alkyldiazo, $C_5$-$C_6$ aryldiazo, trifluoromethyl, $C_1$-$C_4$ haloalkyl, halomethyl, $C_1$-$C_4$ cyanoalkyl, cyanomethyl, cyano, $C_1$-$C_4$ alkyloxycarbonyl, $C_1$-$C_4$ alkylcarbonyl, phenyl, phenylcarbonyl, formyl, $C_1$-$C_4$ alkoxymethyl, phenoxymethyl, $C_2$-$C_4$ vinyl, $C_2$-$C_4$ ethynyl, and $SO_nR'$ wherein n is 0, 1, 2, or 3 and R' is hydrogen, $C_1$-$C_4$ alkyl, amino, or phenyl;

and $R_3$ is selected from the group consisting of hydrogen, $C_1$-$C_4$ alkyl, $C_1$-$C_4$ aminoalkyl, $C_1$-$C_4$ hydroxyalkyl, $C_1$-$C_4$ alkylaminoalkyl, $C_1$-$C_4$ dialkylaminoalkyl, $C_1$-$C_4$ cyanoalkyl, $C_1$-$C_4$ carbamoylalkyl, $C_1$-$C_4$ pivaloylalkyl, $C_1$-$C_6$ alkylcarbonyloxy $C_1$-$C_4$ alkyl, $C_1$-$C_4$ alkoxycarbonylalkyl, ribose, 2'-deoxyribose, the conjugate acid form of a $C_1$-$C_4$ carboxyalkyl, and the carboxylate anion of a $C_1$-$C_4$ carboxyalkyl as the sodium salt; or a pharmaceutically acceptable salt thereof;

with the proviso that when $R_1$ and $R_3$ are hydrogen, R cannot be para-aminoalkyl. The compound of formula (I) are inactivators of the AGT.

In the above embodiment, R is preferably meta-amino $C_1$-$C_6$ alkyl. In a particular embodiment, R is meta-amino methyl and $R_1$ and $R_3$ are hydrogen. The inactivators may be used as pharmaceutically acceptable salts as described earlier.

The compounds of formula (I) are advantageous as they have or are expected to have increased solubility in water as they can become positively charged. For example, some of the aminoalkyl substituted $O^6$-benzylguanines are 20 or more times, preferably 100 or more times, specifically hundred or more times, e.g., 700 to 1000 times or more, soluble in water than $O^6$-benzylguanine. Accordingly, they can be administered in simple aqueous formulations that require little or no organic diluents. Organic diluents could be toxic to the brain, for example. They are, therefore, extremely useful for intratumoral administration. Accordingly, these compounds are suitable for use in the treatment of brain cancer, Myelosupression can be limited by the use of these inactivators.

The present invention further provides a pharmaceutical composition comprising an inactivator or prodrug described above and a pharmaceutically acceptable carrier.

Generally, the inactivator or prodrugs of the present invention as described above will be administered in a pharmaceutical composition to an individual afflicted with a cancer. Those undergoing or about to undergo chemotherapy can be treated with the inactivator or prodrugs separately or in conjunction with other treatments, as appropriate. In therapeutic applications, compositions are administered to a patient in an amount sufficient to elicit an effective depression of AGT activity thereby potentiating the cytotoxicity of the chemotherapeutic treatment. An amount adequate to accomplish this is defined as a "therapeutically effective dose," which is also an "AGT inactivating effective amount." Amounts effective for a therapeutic or prophylactic use will depend on, e.g., the stage and severity of the disease being treated, the age, weight, and general state of health of the patient, and the judgment of the prescribing physician. The size of the dose will also be determined by the prodrug selected, method of administration, timing and frequency of administration as well as the existence, nature, and extent of any adverse side-effects that might accompany the administration of a particular prodrug and the desired physiological effect. It will be appreciated by one of skill in the art that various disease states may require prolonged treatment involving multiple administrations, perhaps using a series of different prodrugs of AGT inactivators and/or chemotherapeutic agents in each or various rounds of administration.

Suitable chemotherapeutic agents administered in coordination with the inactivators or prodrugs of the present invention include alkylating agents, such as chloroethylating and methylating agents. Such agents may be administered using techniques such as those described in Wasserman et al., *Cancer*, 3, pp. 1258-1268 (1975) and *Physicians' Desk Reference*, 58th ed., Thomson PDR (2004). For example, 1,3-bis(2-chloroethyl)-1-nitrosourea (carmustine or BCNU, Bristol-Myers, Evansville, Ind.) may be administered intravenously at a dosage of about 40 mg/m$^2$ when O$^6$-benzylguanine is employed. Other alkylating agents may be administered in appropriate dosages via routes of administration known to skilled medical practitioners.

Suitable doses and dosage regimens can be determined by conventional range-finding techniques known to those of ordinary skill in the art. Generally, treatment is initiated with smaller dosages that are less than the optimum dose of the prodrug. Thereafter, the dosage is increased by small increments until the optimum effect under the circumstances is reached. The present inventive method may involve the administration of about 0.1 µg to about 50 mg of one or more of the prodrugs per kg body weight of the individual. For a 70 kg patient, dosages of from about 10 µg to about 200 mg of the prodrug would be more commonly used, depending on a patient's physiological response, as determined by measuring cancer-specific antigens or other measurable parameters related to the tumor load of a patient.

The inactivators, prodrugs and compositions of the present invention may be employed in many disease states including life-threatening or potentially life-threatening situations. In view of the relatively less toxic nature of the inactivator or prodrug, it is possible and may be felt desirable by the treating physician to administer some or substantial excess of the prodrug. Single or multiple administrations of the inactivator or prodrug can be carried out with dose levels and pattern being selected by the treating physician. In any event, the pharmaceutical formulations should provide a quantity of AGT-inactivating compound or prodrug of the invention sufficient to effectively enhance the cytotoxic impact of the chemotherapy.

The pharmaceutical compositions for therapeutic treatment are intended for parenteral, topical, oral or local administration and generally comprise a pharmaceutically acceptable carrier and an amount of the active ingredient sufficient to reduce, and preferably prevent, the activity of the AGT protein. The carrier may be any of those conventionally used and is limited only by chemico-physical considerations, such as solubility and lack of reactivity with the prodrug, and by the route of administration.

The pharmaceutically acceptable carrier (or excipient) is preferably one that is chemically inert to the inactivator or the prodrug or its active compound and one that has no detrimental side effects or toxicity under the conditions of use. Such pharmaceutically acceptable carriers preferably include saline (e.g., 0.9% saline), Cremophor EL (which is a derivative of castor oil and ethylene oxide available from Sigma Chemical Co., St, Louis, Mo.) (e.g., 5% Cremophor EL/5% ethanol/90% saline, 10% Cremophor EL/90% saline, or 50% Cremophor EL/50% ethanol), propylene glycol (e.g., 40% propylene glycol/10% ethanol/50% water), polyethylene glycol (e.g., 40% PEG400/60% saline), and alcohol (e.g., 40% ethanol/60% water). A preferred pharmaceutical carrier is polyethylene glycol, such as PEG 400, and particularly a composition comprising 40% PEC 400 and 60% water or saline. The choice of carrier will be determined in part by the particular prodrug chosen, as well as by the particular method used to administer the composition. Accordingly, there is a wide variety of suitable formulations of the pharmaceutical composition of the present invention.

The following formulations for oral, aerosol, parenteral, subcutaneous, intravenous, intraarterial, intramuscular, interperitoneal, rectal, and vaginal administration are merely exemplary and are in no way limiting. The pharmaceutical compositions can be administered parenterally, e.g., intravenously, intraarterially, subcutaneously, intradermally, or intramuscularly. Thus, the invention provides compositions for parenteral administration that comprise a solution of the prodrug dissolved or suspended in an acceptable carrier suitable for parenteral administration, including aqueous and non-aqueous, isotonic sterile injection solutions.

Overall, the requirements for effective pharmaceutical carriers for parenteral compositions are well known to those of ordinary skill in the art. See *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986). Such compositions include solutions containing antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The prodrug may be administered in a physiologically acceptable diluent in a pharmaceutical carrier, such as a sterile liquid or mixture of liquids, including water, saline, aqueous dextrose and related sugar solutions, an alcohol, such as ethanol, isopropanol (for example in topical applications), or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, and synthetic oils. Specific examples of oils useful in such formulations include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl-β-aminopropionates, and 2-alkyl-imidazoline quaternary ammonium salts, and (e) mixtures thereof.

The parenteral formulations typically will contain from about 0.5% or less to about 25% or more by weight of the active ingredient or prodrug in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Topical formulations, including those that are useful for transdermal drug release, are well known to those of skill in the art and are suitable in the context of the present invention for application to skin.

Formulations suitable for oral administration can consist of (a) liquid solutions, such as an effective amount of the inactivator or prodrug dissolved in diluents, such as water, saline, or orange juice; (b) capsules, sachets, tablets, lozenges, and troches, each containing a predetermined amount of the prodrug, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising a prodrug in an inert base, such as gelatin and glycerin, or sucrose and acacia, emulsions, gels, and the like containing, in addition to the prodrug, such excipients as are known in the art.

The inactivators or prodrugs of the present invention, alone or in combination with other suitable components, can be made into aerosol formulations to be administered via inhalation. The inactivators or prodrugs are preferably supplied in finely divided form along with a surfactant and propellant. Typical percentages of active inactivator or prodrug may be about 0.01% to about 20% by weight, preferably about 1% to about 10% by weight, The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute from about 0.1% to about 20% by weight of the composition, preferably from about 0.25% to about 5%. The balance of the composition is ordinarily propellant. A carrier can also be included as desired, e.g., lecithin for intranasal delivery. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Additionally, the inactivators or prodrugs may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The concentration of the inactivators or prodrugs of the present invention in the pharmaceutical formulations may vary, e.g., from less than about 1%, usually at or at least about 10%, to as much as 20% to 50% or more by weight, and may be selected primarily by fluid volumes, and viscosities, in accordance with the particular mode of administration selected.

Thus, a typical pharmaceutical composition for intravenous infusion could be made up to contain 250 ml of sterile Ringer's solution, and 100 mg of the inactivator or prodrug. Actual methods for preparing parenterally administrable inactivators or prodrugs will be known or apparent to those skilled in the art and are described in more detail in, for example, *Remington's Pharmaceutical Science* (17th ed., Mack Publishing Company, Easton, Pa., 1985).

It will be appreciated by one of ordinary skill in the art that, in addition to the aforedescribed pharmaceutical compositions, the inactivators or prodrugs of the present inventive method may be formulated as inclusion complexes, such as cyclodextrin inclusion complexes, or liposomes. Liposomes may serve to target the inactivators or prodrugs to a particular tissue, such as lymphoid tissue or cancerous hepatic cells. Liposomes can also be used to increase the half-life of the prodrug. Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837,028, and 5,019,369.

The present invention has applicability to the treatment of any type of cancer capable of being treated with an antineoplastic alkylating agent which causes cytotoxic lesions at the $O^6$-position of guanine. Such cancers include, for example, colon tumors, prostate tumors, brain tumors, lymphomas, leukemias, breast tumors, ovarian tumors, lung tumors, Wilms' tumor, rhabdomyosarcoma, multiple myeloma, stomach tumors, soft-tissue sarcomas, Hodgkin's disease, and non-Hodgkin's lymphomas.

The present invention further provides a method of enhancing the chemotherapeutic treatment of tumor cells in a mammal with an antineoplastic alkylating agent that causes cytotoxic lesions at the $O^6$-position of guanine, which method comprises administering to a mammal an effective amount of the inactivator or prodrug described above and administering to said mammal an effective amount of an antineoplastic alkylating agent which causes cytotoxic lesions at the $O^6$-position of guanine. In a specific embodiment, the tumor cells are necrotic tumor cells which express a β-glucuronidase enzyme. For example, in ovarian, breast, stomach, lung, and bowel carcinomas—necrosis produces β-glucuronidase enzyme.

The inactivator or prodrug can be administered as part of prodrug monotherapy (PMT); Bosslet et al., *Tumor Targeting* 1995, 1, 45-50; deGroot et al., *Curr. Med. Chem.* 2001, 8, 1093-1122. If the tumor cell does not produce a β-glucuronidase enzyme, the enzyme can be administered to the patient, for example, by a targeted delivery. In an embodiment, the β-glucuronidase enzyme can be administered to the patient as a conjugate, such as a conjugate of a humanized F(ab')2 fragment of an anti-CEA antibody and of human β-glucuronidase (see, e.g., U.S. Pat. No. 5,955,100) or alternatively, by the ADEPT system (U.S. Pat. No. 5,935,995;

Bagshawe et al., *Br. J. Cancer* 1988, 58, 700-703), which is a two-step system in which in a first step an antibody-enzyme conjugate (AEC) is injected intravenously. The AEC is retained in the tumor on account of its tumor selectivity, but excreted from healthy tissues in the course of 2-7 days. The prodrug injected intravenously in the second step is activated to give the drug in the tumor by the enzymatic activity of the AEC. As a consequence of the tumor specific activation, increased drug concentrations are observed in tumor and lower drug concentrations are observed in the healthy tissue in comparison with the standard therapy. The FMPA concept (fusion protein-mediated prodrug activation, U.S. Pat. No. 5,935,995) works similarly to the ADEPT system, in which, instead of the xenogeneic and therefore immunogenic AEC, a nonimmunogenic human fusion protein is employed for the tumor selective prodrug activation. In the VDEPT system (vector-dependent enzyme prodrug therapy, U.S. Pat. No. 5,935,995) a two-step recombinant DNA mixture, prodrugs are also activated in a tumor-selective manner after injection of a vector and expression of a structural gene which codes for an enzyme.

The present invention also provides a method of enhancing the effect of an antineoplastic alkylating agent, which alkylates the $O^6$-position of guanine residues in DNA, in the chemotherapeutic treatment of cancer in a mammal, particularly a human. The method comprises co-administering to the mammal a cancer-treatment effective amount of an antineoplastic alkylating agent and a chemotherapeutic treatment-enhancing amount of an inactivator or prodrug in accordance with the present invention.

In an embodiment, the invention provides a method of enhancing the chemotherapeutic treatment of tumor cells in a mammal with an antineoplastic alkylating agent that causes cytotoxic lesions at the $O^6$-position of guanine, which method comprises administering to a mammal an effective amount of the compound of formula (I) and administering to the mammal an effective amount of an antineoplastic alkylating agent which causes cytotoxic lesions at the $O^6$-position of guanine,

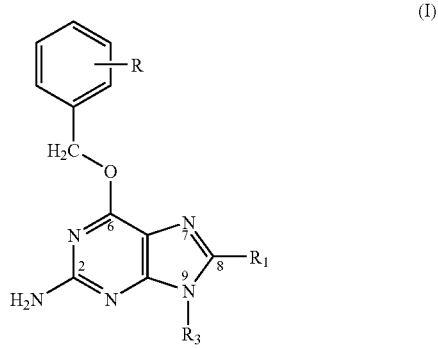

(I)

wherein R is amino $C_1$-$C_6$ alkyl;

$R_1$ is selected from the group consisting of hydrogen, halo, $C_1$-$C_4$ alkyl, $C_1$-$C_4$ hydroxyalkyl, thiol, $C_1$-$C_4$ alkylthio, trifluoromethylthio, $C_1$-$C_4$ thioacyl, hydroxy, $C_1$-$C_4$ alkoxy, trifluoromethoxy, methanesulfonyloxy, trifluoromethanesulfonyloxy, $C_1$-$C_4$ acyloxy, amino, $C_1$-$C_4$ aminoalkyl, $C_1$-$C_4$ alkylamino, $C_1$-$C_4$ dialkylamino, trifluoromethylamino, ditrifluoromethylamino, aminomethanesulfonyl, $C_1$-$C_4$ aminoacyl, aminotrifluoromethylcarbonyl, formylamino, nitro, nitroso, $C_1$-$C_4$ alkyldiazo, $C_5$-$C_6$ aryldiazo, trifluoromethyl, $C_1$-$C_4$ haloalkyl, halomethyl, $C_1$-$C_4$ cyanoalkyl, cyanomethyl, cyano, $C_1$-$C_4$ alkyloxycarbonyl, $C_1$-$C_4$ alkylcarbonyl, phenyl, phenylcarbonyl, formyl, $C_1$-$C_4$ alkoxymethyl, phenoxymethyl, $C_2$-$C_4$ vinyl, $C_2$-$C_4$ ethynyl, and $SO_nR'$ wherein n is 0, 1, 2, or 3 and R' is hydrogen, $C_1$-$C_4$ alkyl, amino, or phenyl;

and $R_3$ is selected from the group consisting of hydrogen, $C_1$-$C_4$ alkyl, $C_1$-$C_4$ aminoalkyl, $C_1$-$C_4$ hydroxyalkyl, $C_1$-$C_4$ alkylaminoalkyl, $C_1$-$C_4$ dialkylaminoalkyl, $C_1$-$C_4$ cyanoalkyl, $C_1$-$C_4$ carbamoylalkyl, $C_1$-$C_4$ pivaloylalkyl, $C_1$-$C_6$ alkylcarbonyloxy $C_1$-$C_4$ alkyl, $C_1$-$C_4$ alkoxycarbonylalkyl, ribose, 2'-deoxyribose, the conjugate acid form of a $C_1$-$C_4$ carboxyalkyl, and the carboxylate anion of a $C_1$-$C_4$ carboxyalkyl as the sodium salt; or pharmaceutically acceptable salt thereof. In a particular embodiment of the compound of the method, R is para or meta amino methyl and $R_1$ and $R_3$ are hydrogen.

By "enhancing the effect of an antineoplastic alkylating agent" is meant that the antineoplastic alkylating agent has a greater effect in the presence of an inactivator or prodrug of the present invention than in the absence of the inactivator or prodrug. When an alkyltransferase acts on the inactivator released from the prodrug, it is inactivated and, therefore, is not able to act on the DNA in a cancerous cell that has been alkylated by the antineoplastic alkylating agent. Given that the alkyltransferase is not able to act on the alkylated DNA in a cancerous cell, the DNA in the cancerous cell is not repaired, thereby leading to death of the cancerous cell.

By "coadministering" is meant administering the antineoplastic alkylating agent and the prodrug sufficiently close in time such that the inactivator or prodrug can enhance the effect of the antineoplastic alkylating agent. In this regard, the inactivator or prodrug can be administered first and the antineoplastic alkylating agent can be administered second, or vice versa. Alternatively, the inactivator or prodrug and the antineoplastic alkylating agent can be administered simultaneously. In addition, a combination of inactivators and prodrugs can be administered, and one or more of the inactivators or prodrugs can be administered in combination with another agent useful in the treatment of cancer.

The antineoplastic alkylating agent is administered in a dose sufficient to treat the cancer (e.g., cancer-treatment effective amount of an antineoplastic alkylating agent). Such doses are known in the art (see, for example, the *Physicians' Desk Reference* (2004)). For example, 1,3-bis(2-chloroethyl)-1-nitrosourea (carmustine or BCNU, Bristol-Myers, Evansville, Ind.) can be administered intravenously to a patient at a dosage of from about 150 to 200 mg/m² every six weeks. Another alkylating agent, namely 1-(2-chloroethyl)-3-cyclohexyl-1-nitrosourea (lomustine or CCNU, Bristol-Myers), can be administered orally at a dosage of about 130 mg/m² every six weeks.

The inactivator or prodrug is administered in a dose sufficient to enhance the effect of the antineoplastic alkylating agent (e.g., chemotherapeutic treatment-enhancing amount). A suitable dosage is that which will result in a concentration of the inactivator or prodrug in the cancerous cells to be treated sufficient to deplete alkyltransferase activity, e.g., from about 10 nM to 200 nM intracellularly, which may require an extracellular concentration of from about 10 μM to 50 μM. The dose can be adjusted as necessary to enhance the effect of the antineoplastic alkylating agent.

The inactivators or prodrugs of the present invention are useful in enhancing the effect of any suitable antineoplastic alkylating agent that alkylates the $O^6$-position of guanine residues in DNA. Examples of antineoplastic alkylating agents include chloroethylating agents. The most frequently used chloroethylating agents include 1-(2-chloroethyl)-3-cyclohexyl-1-nitrosourea (CCNU, lomustine), 1,3-bis(2-chloroethyl)-1-nitrosourea (BCNU, carmustine), 1-(2-chloroethyl)-3-(4-methylcyclohexyl)-1-nitrosourea (MeCCNU, semustine), and 1-(2-chloroethyl)-3-(4-amino-2-methyl-5-pyrimidinyl)methyl-1-nitrosourea (ACNU). Such agents have been used clinically against tumors of the central nervous system, multiple myeloma, melanoma, lymphoma, gastrointestinal tumors, and other solid tumors (Colvin and Chabner. Alkylating Agents. In: *Cancer Chemotherapy: Principles and Practice*. Edited by B. A. Chabner and J. M. Collins, Lippincott, Philadelphia, Pa. pp. 276-313 (1990); and McCormick et al., *Eur. J. Cancer* 26: 207-221 (1990)). Chloroethylating agents, which have fewer side effects and are currently under development include 1-(2-chloroethyl)-3-(2-hydroxyethyl)-1-nitrosourea (HECNU), 2-chloroethylmethylsulfonylmethanesulfonate (Clomesone), and 1-[N-(2-chloroethyl)-N-nitrosoureido]ethylphosphonic acid diethyl ester (Fotemustine) (Colvin and Chabner (1990), supra; and McCormick et al. (1990), supra). Methylating agents include Streptozotocin (2-deoxy-2-(3-methyl-3-nitrosoureido)-D-glucopyranose), Procarbazine (N-(1-methylethyl)-4-[(2-methylhydrazino)methyl]benzamide), Dacarbazine or DTIC (5-(3,3-dimethyl-1-triazenyl)-1H-imidazole-4-carboxamide), and Temozolomide (8-carbamoyl-3-methylimidazo[5.1-d]-1,2,3,5-tetrazin-4-(3H)-one).

Temozolomide is active against malignant melanomas, brain tumors and mycosis fungoides. Streptozotocin is effective against pancreatic tumors. Procarbazine is used to treat Hodgkin's disease and brain tumors. DTIC is used to treat melanoma and lymphomas (Colvin and Chabner (1990), supra; and Longo, *Semin. Concol.* 17; 716-735 (1990)).

The antineoplastic alkylating agent can be administered by any route. Conventional means of administration are described in Wasserman et al. (*Cancer* 36: 1258-1268 (1975)) and in *Physicians' Desk Reference* (2004).

The inactivators of AGT, e.g., unsubstituted or substituted $O^6$-benzylguanine, unsubstituted or substituted $O^6$-benzyl-2'-deoxyguanosine, $O^6$-benzyl-8-azaguanine, $O^6$-benzyloxy pyrimidine, and $O^6$-benzyloxy-s-triazine can be prepared by methods known to those skilled in the art; see, Moschel et al. patents, e.g., U.S. Pat. Nos. 5,091,430; 5,525,606; and 5,958,932, above.

The prodrugs of the invention can be prepared by any suitable method. By way of illustration, prodrugs 1 and 2 can be prepared in accordance with the reactions shown in Scheme 1.

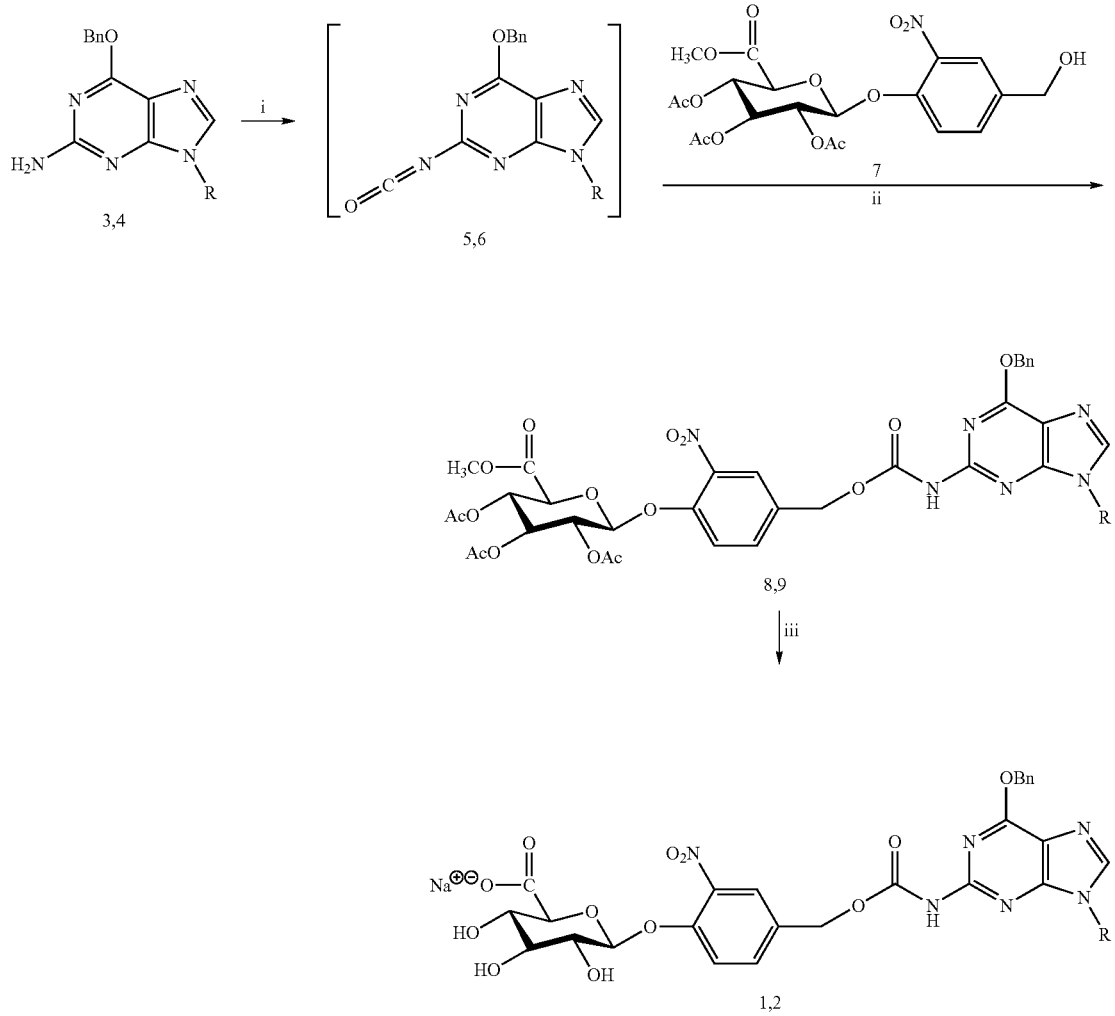

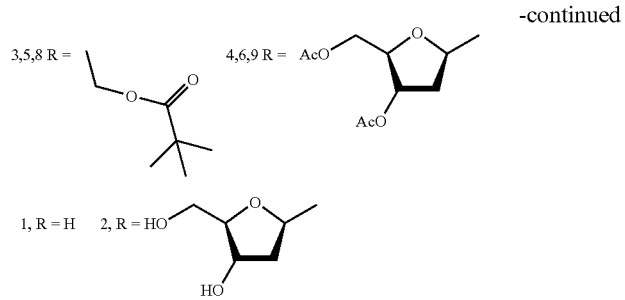

Scheme 1. Reagents and conditions: (i) phosgene, CH$_2$Cl$_2$/pyridine, 0° C. to rt, 20 h; (ii) rt, 2 h; (iii) MeOH/2 N NaOH (1:1), 0° C., 30 min, followed by neutralization with 10% acetic acid.

The starting material for prodrug 1 is O$^6$-benzyl-9-[(pivaloyloxy)methyl]guanine (3) and the starting material for prodrug 2 is 3',5'-di-O$^6$-acetyl-O$^6$-benzyl-2'-deoxyguanosine (4). When 3 or 4 is reacted with an equivalent of phosgene, unstable intermediates, presumably the isocyanates 5 and 6, respectively, are produced. These are reacted individually without isolation with 4-O-(2',3',4'-tri-O-acetyl-6'-methyl-β-D-glucopyranuronosyl)-3-nitrobenzyl alcohol (7) in one pot to produce the respective coupled products 8 and 9. Deprotection of these derivatives with methanolic sodium hydroxide and neutralization with 10% acetic acid lead to the formation of viscous colloidal suspensions which are slowly suction-filtered to produce crude samples or either 1 or 2. Analytically pure samples of 1 and 2 are obtained after purification by Sephadex LH-20 column chromatography and lyophilization.

Prodrugs containing other AGT inactivators can be prepared by an analogous method. For example, the inactivator such as a O$^6$-benzyl-9-[(pivaloyloxy)methyl]-8-azaguanine can be reacted with phosgene. The 2-position substituent of the inactivator is preferably an amino group to enable the reaction with phosgene.

The following examples further illustrate the present invention. The examples, of course, should not be construed as in any way limiting the scope of the present invention.

Example 1

This example illustrates a method of synthesis of prodrugs in accordance with an embodiment of the invention.

3',5'-Di-O-acetyl-2'-deoxyguanosine was synthesized by the method of Schaller, et al., *J. Amer. Chem. Soc.*, 1963, 85, 3821-3827. Previously unreported spectroscopic data for this compound are presented below. Unless otherwise stated, all other chemicals were obtained from Sigma or Aldrich and were used without further purification. Melting points were determined using an electrothermal apparatus and are uncorrected. $^1$H-NMR spectra were recorded in the indicated solvent with a Varian INOVA 400 MHz spectrometer. Chemical shifts are reported as δ values in ppm relative to TMS as internal standard. Mass spectra were obtained on a Thermo Finnigan TSQ Quantum LC mass spectrometer using electrospray ionization (ESI) and measuring either positive or negative ions. Elemental analyses were performed by Atlantic Microlab.

3',5'-Di-O-acetyl-2'-deoxyguanosine. 2'-Deoxyguanosine (Syngen, Inc.) (5.03 g, 17.6 mmol) was twice evaporated from 30 mL anhydrous pyridine and was suspended in 200 mL dry pyridine. Acetic anhydride (30 mL, 317 mmol) was added and the mixture was stirred at room temperature for 3 days. The resulting suspended solid was collected by filtration and rinsed with ethyl ether to afford 5.73 g (93%) of 3',5'-di-O-acetyl-2'-deoxyguanosine. $^1$H-NMR δ$_H$(DMSO-d) 10.67 (s, 1H, H-1, exchanges with D$_2$O), 7.91 (s, 1H, H-8), 6.50 (s, 2H, N$^2$H$_2$ exchange with D$_2$O), 6.13 (dd, J=6.0, J'=8.7, 1H, H-1'), 5.30-5.29 (m, 1H, H-3'), 4.29-4.24 (m, 1H, H-4'), 4.21-4.16 (m, 2H, H-5'), 2.95-2.88 (m, 1H, H-1'α), 2.48-2.42 (m, 1H, H-2'β), 2.08 and 2.04 (two s, 6H, 2COCH$_3$).

3',5'-Di-O-acetyl-O$^6$-benzyl-2'-deoxyguanosine (4) was prepared following the method of Zajc et al., *Tet. Lett.* 1992, 33, 3409-3412. To a mixture of 3',5'-di-O-acetyl-2'-deoxyguanosine (5.71 g, 16.3 mmol), triphenylphosphine (5.91 g, 22.5 mmol) and benzyl alcohol (2.5 mL, 24.1 mmol) in 100 mL 1,4-dioxane under argon was slowly added diisopropylazodicarboxylate (4.5 mL, 22.8 mmol). The mixture was heated to 85° C. for two hr and was then cooled and concentrated to a thick paste on a rotary evaporator. The product was isolated as a light brown solid (1.78 g, 24.8%) following silica gel column chromatography with 10% ethyl acetate/chloroform. $^1$H-NMR δ$_H$(DMSO-d$_6$) 8.09 (s, 1H, H-8), 7.51-7.35 (m, 5H, Ar), 6.54 (s, 2H, N$^2$H$_2$, exchange with D$_2$O), 6.24 (dd, J=6.0, J'=8.5, 1H, H-1'), 5.50 (s, 2H, OCH$_2$Ar), 5.33-5.32 (m, 1H, H-3'), 4.32-4.27 (m, 1H, H-4'), 4.22-4.18 (m, 2H, H-5'), 3.06-2.98 (m, 1H, H-2'α), 2.50-2.44 (m, 1H, H-2'β), 2.09 (s, 3H, COCH$_3$), 2.02 (s, 3H, COCH$_3$); MS, m/z 442.1 [M+H]$^+$, 464.1 [M+Na]$^+$; Anal. Calcd. for C$_{21}$H$_{23}$N$_5$O$_6$: C, 57.14; H, 5.25; N, 15.86.

Found: C, 57.50; H, 5.31; N, 15.40.

O$^6$-Benzyl-N$^2$-[[[[4'-[(2",3",4"-tri-O-acetyl-6"-methyl-β-D-glucopyranuronosyl)oxy]-3'-nitrophenyl]methyl]oxy]carbonyl]-9-[(pivaloyloxy)methyl]guanine (8). To an ice-cooled solution of O$^6$-benzyl-9-[(pivaloyloxy)methyl]guanine (3) (Chae et al., *J. Med. Chem.*, 1981, 24, 479-480) (1.97 g, 5.5 mmol) in 120 mL anhydrous dichloromethane and 5 mL pyridine was added a toluene solution of phosgene (2.8 mL, 5.3 mmol phosgene) and the mixture was stirred for 20 hr while the ice bath was allowed to warm to room temperature. A solution of 4-O-(2',3',4'-tri-O-acetyl-6'-methyl-β-D-glucopyranuronosyl)-3-nitrobenzyl alcohol (7) (Florent et al., *J. Med. Chem.*, 1998, 41, 3572-3581) (2.31 g, 4.8 mmol) in 150 mL dichloromethane was then added and the solution was stirred at room temperature for 2 hr. Purification by flash column chromatography (ethyl acetate:chloroform, 3:7) gave 8 (2.02 g, 42%). $^1$H-NMR δ$_H$(DMSO-d$_6$) 10.63 (s, 1H, N$^2$H, exchanges with D$_2$O), 8.29 (s, 1H, H-8), 8.03 (d, 1H, O$_2$NArH-2'), 7.79 (dd, J=8.8, J'=2.1, 1H, O$_2$NArH-6'), 7.59 (dd, 2H, Ar), 7.46 (d, J 8.7, 1H, O$_2$NArH-5'), 7.41-7.35 (m, 3H, Ar-m, p), 6.08 (s, 2H, 9-CH$_2$), 5.75 (d, J 7.8, 1H, H-1"), 5.61 (s, 2H, OCH$_2$Ar), 5.46 (t, J 9.6, 1H, H-2"), 5.23 (s, 2H, O₂NArCH₂), 5.15-5.08 (m, 2H, H-3''',4''), 4.75 (d, J 9.9, 1H, H-5''), 3.64 (s, 3H, CH₃), 2.02-2.00 (3 s, 9H, 3 COCH₃), 1.09 (s, 9H, C(CH₃)₃); MS m/z 867.5 [M+H]⁺, 889.4 [M+Na]⁺; Anal. Calcd. for C₃₉H₄₂N₆O₁₇: C, 54.04; H, 4.88; N, 9.70. Found: C, 54.17; H, 5.06; N, 9.64.

3',5'-Di-O-acetyl-O⁶-benzyl-N²-[[[[4''-[(2''',3''',4'''-tri-O-acetyl-6'''-methyl-β-D-glucopyranuronosyl)oxy]-3''-nitrophenyl]methyl]oxy]carbonyl]-2'-deoxyguanosine (9). Using the above procedure for compound 8, compound 9 was obtained in 54% yield. ¹H-NMR δ$_H$(DMSO-d₆) 10.56 (s, 1H, N²H, exchanges with D₂O), 8.39 (s, 1H, H-8), 8.02 (d, J=2.1, 1H, O₂NArH-2''), 7.78 (dd, J=8.7, J'=2.1, 1H, O₂NArH-6''), 7.55 (dd, J=8.1, J'=1.7, 2H, Ar-o), 7.46 (d, J=8.7, 1H, O₂NArH-5''), 7.41-7.35 (m, 3H, Ar-m, p), 6.35 (dd, J=6.5, J'=7.5, 1H, H-1'), 5.75 (d, J=7.8, 1H, H-1'''), 5.61 (s, 2H, CH₂Ar), 5.50-5.41 (m, 2H, H-2''' and H-3'), 5.22 (s, 2H, O₂NArCH₂), 5.15-5.08 (m, 2H, H-3''',4''), 4.74 (d, J=9.8, 1H, H-5'''), 4.36-4.31 (m, 1H, H-4'), 4.26-4.22 (m, 2H, H-5'), 3.64 (s, 3H, CH₃) 3.29-3.20 (m, 1H, H-2'α), 2.54-2.51 (m, 1H, H-2'β), 2.09-1.98 (5s, 15H, 5 COCH₃); MS m/z 953.2 [M+H]⁺, 975.1 [M+Na]⁺; Anal. Calcd. for C₄₂H₄₄N₆O₂₀; C, 52.94; H, 4.65; N, 8.82. Found: C, 52.84; H, 4.70; N, 8.48.

O⁶-Benzyl-N-[[[[4'-[(-β-D-glucopyranuronosyl)oxy]-3'-nitrophenyl]methyl]oxy]carbonyl]guanine, monosodium salt (1). To a ice-cooled solution of 8 (0.424 g, 0.49 mmol) in 10 mL methanol was added 10 mL of an ice-cooled solution of 2 M sodium hydroxide and the mixture was stirred at 0° C. for 30 min. The solution was neutralized with 10% acetic acid to produce a viscous suspension that was slowly suction filtered (Whatman #50 filter paper) and allowed to dry. The crude product was purified on a Sephadex LH-20 column eluted with H₂O:methanol (65:35) at a flow rate of 1 mL/min. UV absorption was continuously monitored at 254 nm and fractions (10 mL) were collected. The product (1) eluted in fractions 40-50. Methanol was removed on a rotary evaporator at room temperature. The resulting aqueous solution was lyophilized to provide 1 as a white solid (0.210 g, 64%), UV [0.05M phosphate buffer (pH7.0)] λ$_{max}$=267 (ε=1.32×10⁴ M⁻¹·cm⁻¹); ¹H-NMR δ$_H$(D₂O, DSS internal standard) 8.00 (s, 1H, H-8), 7.49-7.06 (m, 8H, Ar), 5.36 (s, 2H, OCH₂Ar), 5.04 (d, J=6.9, 1H, H-1''), 4.91 (s, 2H, O₂NArCH₂), 3.86 (d, J=9.2, 1H, H-5''), 3.68-3.61 (m, 3H, H-2'',3'',4''); δ$_H$(DMSO-d₆) 10.34 (s, 1H, N²H, exchanges with D₂O), 8.15 (s, 1H, H-8), 7.97 (d, J=2.1, 1H, O₂NArH-2'), 7.71 (dd, J=9.0, J'=2.1, 1H, O₂NArH-6'), 7.57 (dd, J=8.2, J'=1.6, 2H, Ar-o), 7.45 (d, J=8.7, 1H, O₂NArH-5'), 7.41-7.35 (m, 3H, Ar-m, p), 7.26 (broad s, 1H, H-9, exchanges with D₂O), 5.59 (s, 2H, O₂NArCH₂), 5.23 (d, J=4.6, 1H, OH-2'', exchanges with D₂O), 5.18 (s, 2H, CH₂Ar), 5.08 (d, J=7.3, 1H, H-1''), 5.01 (d, J=4.5, 1H, OH-3''), 3.47 (d, J=10.0, 1H, H-5''), 3.26-3.11 (m, 4H, OH-4'' and H-2'',3'',4''); MS [LC (0.1% HCOOH)] m/z 613.2 [M(acid form)+H]⁺, 635.2 [M(acid form)+Na]⁺; Anal. Calcd. for C₂₆H₂₃N₆NaO₁₂·2H₂O: C, 46.57; H, 4.06; N, 12.53. Found: C, 46.52; H, 3.98; N, 12.33.

O⁶-Benzyl-N²-[[[[4''-[(β-D-glucopyranuronosyl)oxy]-3''-nitrophenyl]methyl]oxy]carbonyl]-2'-deoxyguanosine, monosodium salt (2). Using the above procedure for 1, compound 2, which eluted from the Sephadex LH-20 column in fractions 35-48 was obtained in 64% yield. UV [0.05M phosphate buffer (pH 7.0)] λ$_{max}$ 267 (ε=1.97×10⁴ M⁻¹·cm⁻¹); ¹H-NMR δ$_H$(DMSO-d₆) 10.49 (s, 1H, N²H, exchanges with D₂O), 8.40 (s, 1H, H-8), 7.97 (d, J=2.1, 1H, O₂NArH-2''), 7.73 (dd, J=8.8, J'=2.2, 1H, O₂NArH-6''), 7.56 (dd, J=8.2, J'=1.7, 2H, Ar-o), 7.48 (d, J=8.8, 1H, O₂NArH-5''), 7.41-7.35 (m, 3H, Ar-m, p), 7.19 (broad, 1H, OH-2''', exchanges with D₂O), 6.31 (t, J=7.1, 1H, H-1'), 5.60 (s, 2H, O₂NArCH₂), 5.43 (d, J=3.9, 1H, OH-3', exchanges in D₂O), 5.23 (d, J=4.7, 1H, OH-3'''), exchanges with D₂O), 5.20 (s, 2H, CH₂Ar), 5.08 (d, J=7.3, 1H, H-1'''), 5.01 (d, J=4.8, 1H, OH-4''', exchanges with D₂O), 4.89 (t, J=5.4, 1H, OH-5'), 4.41-4.39 (m, 1H, H-3'), 3.87-3.84 (m, 1H, H-4'), 3.61-3.50 (m, 2H, H-5'), 3.47 (d, J=9.9, 1H, H-5'''), 3.29-3.11 (m, 3H, H-2''',3''',4'''), 2.75-2.68 (m, 1H, H-2'α), 2.29-2.23 (m, 1H, H-2'β); MS [LC (H₂O oacetonitrile)] m/z 727.1 [M–Na]⁻; Anal. Calcd. For C₃₁H₃₁N₆NaO₁₅·1.5H₂O; C, 47.88; H, 4.41; N, 10.81. Found: C, 47.90; H, 4.29; N, 10.73.

Example 2

This example illustrates the stability and enzymatic hydrolysis properties of the prodrugs in accordance with an embodiment of the invention.

Prodrug purity of the prodrugs was determined by HPLC on a Hewlett-Packard LC 1090 Series II system equipped with a Phenomenex 250×4 mm column (5 µm particle size) eluted isocratically at 1 mL/min with acetonitrile/0.1 M triethylammonium acetate (TEAA), pH 7.0, (3:7). Aliquots (100 µL) from prodrug solutions were withdrawn and diluted with 100 µL of a solution of p-nitrobenzyl alcohol (an internal standard) in acetonitrile/0.1 M TEAA (6:4). UV detection was at 254 and 280 nm. Retention times for 1, 2, O⁶-benzylguanine, O⁶-benzyl-2'-deoxyguanosine and p-nitrobenzyl alcohol were 5.20, 4.97, 7.13, 7.18 and 8.64 min, respectively. All determinations were carried out in duplicate or triplicate.

The stability of the prodrugs was determined in phosphate buffered saline (pH 7.2) (Life Techologie, Inc), a Tris buffer containing 50 mM Tris-HCl (pH 7.5) (Life Technologies, Inc), 5 mM dithiothreitol and 0.1 mM EDTA, a MOPS buffer (pH 7.0) containing 50 mM morpholinopropane sulfonic acid, 0.01% bovine serum albumin and 0.01% NaCl and a modified Dulbecco's medium prepared by combining 400 mL of Dulbecco's medium with 7 mL of 7.5% NanCO₃, 4 mL of 15 mM glutamine, 2 mL gentamicin and 40 mL of fetal calf serum. Solutions were incubated at 37° C. and prodrug concentrations were analyzed by HPLC at various times as indicated above.

Rate constants for the first-order disappearance of prodrugs were estimated from semi-log plots of the concentration of prodrug as a function of time. Observed first order rate constants for hydrolysis of these prodrugs are presented in Table 1. The spontaneous rate of liberation, for example, in aqueous solutions, of the AGT inactivator is much lower than the rate for β-glucuronidase catalyzed liberation, for example, about 10 times less, and preferably 100 times less. The spontaneous rate of liberation of the AGT inactivator from the prodrug is low, e.g., about 0.2 to about 0.5% by weight per hour.

TABLE 1

Observed First Order Rate Constants (×10⁶, min⁻¹) for Hydrolysis of Prodrugs in Aqueous Buffers

| Prodrug | k$_{PBS}$[a] | k$_{Tris}$[b] | k$_{MOPS}$[c] | k$_{Dulbecco}$[d] |
|---------|------|------|------|------|
| 1 | 3.86 | 4.06 | 3.77 | 4.29 |
| 2 | 0.646 | 0.155 | 0.188 | 0.468 |

[a]PBS = Phosphate buffered saline, pH 7.2;
[b]Tris = 50 mM Tris-HCl (pH 7.5), 5 mM dithiothreitol and 0.1 mM EDTA, pH 7.5;
[c]MOPS = 50 mM morpholinopropane sulfonic acid, pH 7.0, 0.1% bovine serum albumin, 0.01% NaCl;
[d]Dulbecco = modified Dulbecco's medium.

The decomposition of 1 was faster than that of 2 in all buffers although decomposition rates for both compounds are fairly low. For example, under these aqueous conditions, the average half-time for decomposition of 1 is of the order of 100 days.

The enzymatic hydrolysis of the prodrugs was investigated with both *E. coli* and bovine liver β-glucuronidase in MOPS buffer at pH 7.0. Prodrugs and p-nitrobenzyl alcohol (HPLC internal standard) were dissolved in the MOPS buffer (pH 7.0) at 37° C. Enzymatic cleavage was initiated by adding 0.2 Fishman units of *E. coli* β-glucuronidase (Sigma type IX-A) (42.8 units/mg of protein) or 10 Fishman units of bovine liver β-glucuronidase (Sigma type B-10) (10.2 units/mg of protein) to the incubation buffer. Aliquots (100 μL) of the reaction mixture were withdrawn at various times and were mixed with 100 μL of acetonitrile/0.1 M TEAA (6:4) to quench the enzymatic reaction. Prodrug and product concentrations were determined by HPLC. For determination of enzyme kinetic parameters, prodrug solutions at concentrations between 5 and 300 μM were incubated with a fixed amount of enzyme. Aliquots were withdrawn at time intervals varying from 1 to 20 min and the reactions were quenched as described above. Initial reaction velocities were determined at each substrate concentration. Non-linear regression methods were used to determine $K_M$ and $V_{max}$ values. Data were processed with Prism 3.0 software.

Figure 1B:
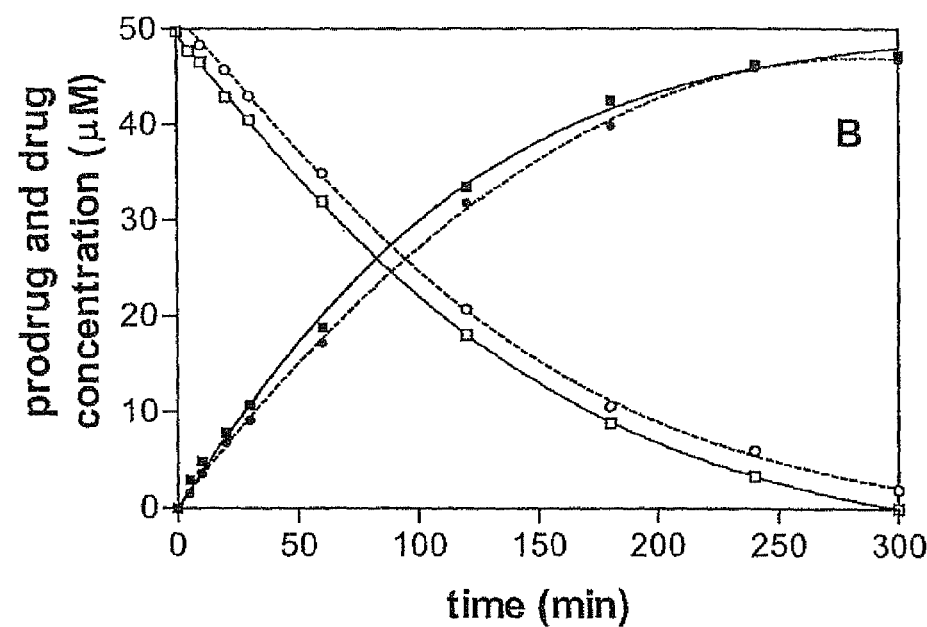
FIG. 1B depicts the concentration of prodrugs 1 (open squares) and 2 (open circles); and the concentration of $O^6$-benzylguanine (closed squares) and $O^6$-benzyl-2'-deoxyguanosine (closed circles), which were produced by the enzymatic cleavage of the prodrugs, as a function of time in contact with 0.2 units/mL *E. coli* β-glucuronidase.

Representative data for hydrolysis of 1 and 2 with the bovine liver enzyme are presented in FIG. 1A. Hydrolysis by the *E. coli* enzyme is shown in FIG. 1B. As indicated, hydrolysis by both the bovine liver enzyme (10 units/mL) or the *E. coli* enzyme (0.2 unit/mL) led to rapid disappearance of both 1 and 2 accompanied by the formation of $O^6$-benzylguanine and $O^6$-benzyl-2'-deoxyguanosine, respectively. Although 1 and 2 were cleaved more rapidly by the *E. coli* protein than the bovine liver protein, and 1 was hydrolyzed more rapidly than 2 by both proteins, the hydrolyses followed Michaelis-Menten kinetics (Table 2) in all cases. These data (Table 2) are comparable to data for other glucuronic acid conjugates such as DOX-GA3 (Houba et al., *Biochem. Pharmacol.* 1996, 52, 455-463) and epicurubicin-glucuronide (Haisma et al., *Br. J. Cancer* 1992, 66, 474-478) although the testing conditions are different.

TABLE 2

Enzyme Kinetic Parameters for Prodrugs[a]

| Prodrug | *E. coli* β-glucuronidase | | bovine liver β-glucuronidase | |
|---|---|---|---|---|
| | $K_M(\mu M)$ | $V_{max}(\mu mol \cdot mg^{-1} \cdot h^{-1})$ | $K_M(\mu M)$ | $V_{max}(\mu mol \cdot mg^{-1} \cdot h^{-1})$ |
| 1 | 17.0 | $4.66 \times 10^5$ | 244 | $1.62 \times 10^4$ |
| 2 | 41.1 | $6.77 \times 10^5$ | 362 | $2.36 \times 10^4$ |

[a]Data obtained at 37° C. in MOPS buffer, pH 7.0.

Example 3

This example illustrates certain properties of prodrugs of the present invention, namely, their ability to inactivate AGT in the presence of β-glucuronidase, and cell killing.

Purified recombinant human alkyltransferase was incubated with different concentrations of prodrugs in 0.5 mL of reaction buffer (50 mM Tris-HCl, pH 7.6, 0.1 mM EDTA, 5.0 mM dithiothreitol) containing 50 μg of hemocyanin for 5 min at 37° C. For experiments involving β-glucuronidase, the bovine liver protein, prodrugs and alkyltransferase were incubated together in the above hemocyanin-containing buffer for 30 min at 37° C. The remaining alkyltransferase activity was determined after incubation with a [$^3$H]-methylated calf thymus DNA substrate for 30 min at 37° C. by measuring the [$^3$H]-methylated methylated protein formed, which was collected on nitrocellulose filters. The results were expressed as the percentage of the alkyltransferase activity remaining. The concentration of inhibitor that led to a 50% loss of alkyltransferase activity ($ED_{50}$) was calculated from graphs of the percentage of remaining alkyltransferase activity against inactivator concentration.

Figure 2A:
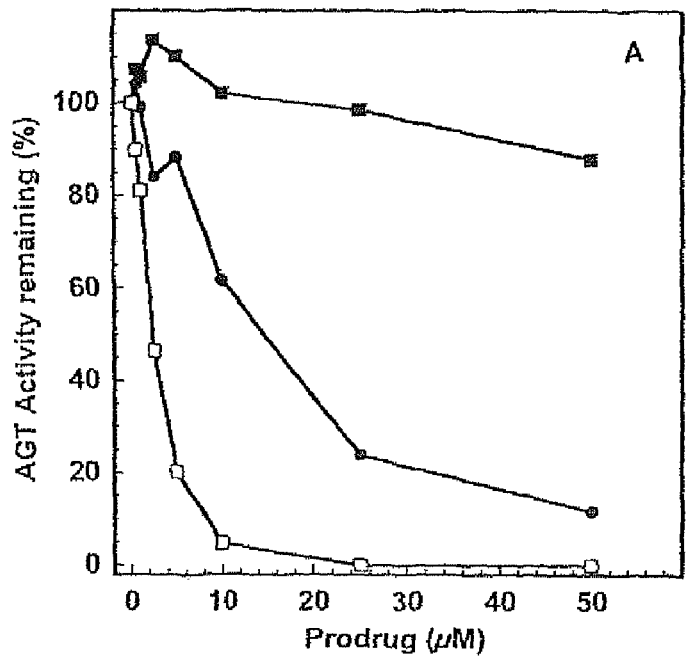
FIG. 2A depicts the % remaining activity of AGT as a function of the concentration of prodrug 1 in the absence of β-glucuronidase (closed squares) and in the presence of bovine liver β-glucuronidase: 20 units/mL of β-glucuronidase (closed circles) and 200 units/mL of β-glucuronidase (open squares).
Figure 2B:
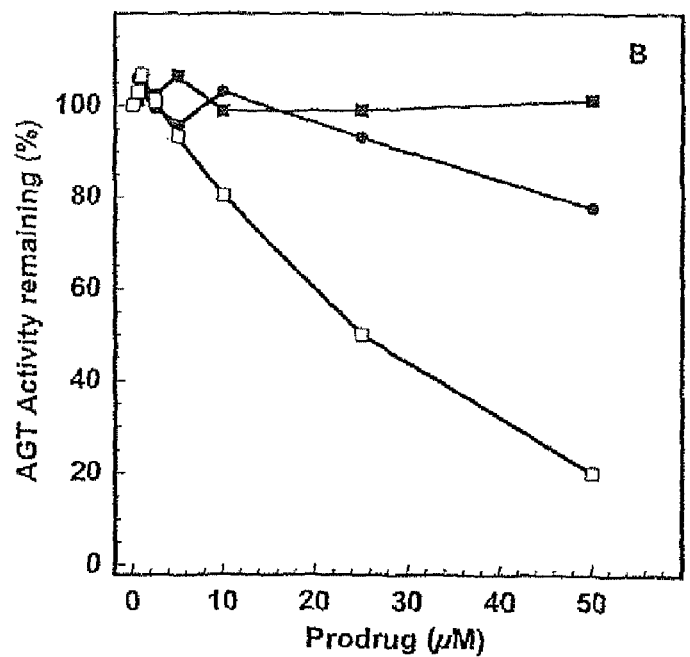
FIG. 2B depicts the % remaining activity of AGT as a function of the concentration of prodrug 2 in the absence of β-glucuronidase (closed squares) and in the presence of bovine liver β-glucuronidase: 20 units/mL of β-glucuronidase (closed circles) and 200 units/mL of β-glucuronidase (open squares).

For inactivation of the human $O^6$-alkylguanine-DNA alkyltransferase, prodrugs 1 and 2 were inactive up to a concentration of 50 μM (FIG. 2) while the $ED_{50}$ for $O^6$-benzylguanine is 0.2 μM (Pegg et al., *Prog. Nucleic Acid Res. Mol. Biol.* 1995, 51, 167-223). This indicates that both 1 and 2 are intrinsically very poor alkyltransferase inactivators compared to $O^6$-benzylguanine. However, incubation of these drugs in the presence of bovine liver β-glucuronidase for 30 min led to efficient alkyltransferase inactivation due to liberation of $O^6$-benzylguanine from 1 (FIG. 2A) or $O^6$-benzyl-2'-deoxyguanosine from 2 (FIG. 2B).

HT29 cells were grown in RPMI 1640 medium in the presence of 10% fetal bovine serum. The effect of alkyltransferase inactivators on the sensitivity of cells to BCNU was determined using a colony-forming assay. Cells were plated at a density of $10^6$ in 25 $cm^2$ flasks and 24 h later were incubated with different concentrations of prodrugs for the time indicated before exposure to 40 μM BCNU for 2 hr. For experiments involving β-glucuronidase, the bovine liver protein was added to the cell cultures at 20 units/mL of medium and incubated along with the prodrug. BCNU was dissolved in absolute ethanol at a concentration of 8 mM. It was diluted with the same volume of ice-cold phosphate-buffered saline, and was immediately administered to cells. After two hr, the medium was replaced with fresh medium and the cells were left to grow for an additional 16-18 h. The cells were then replated at densities of 250 cells per 25 $cm^2$ flask and grown for 8 days until discrete colonies had formed. The colonies were washed with 0.9% saline solution, stained with 0.5% crystal violet in ethanol, and counted. The plating efficiency of cells not treated with drugs was about 50%.

Figure 3:
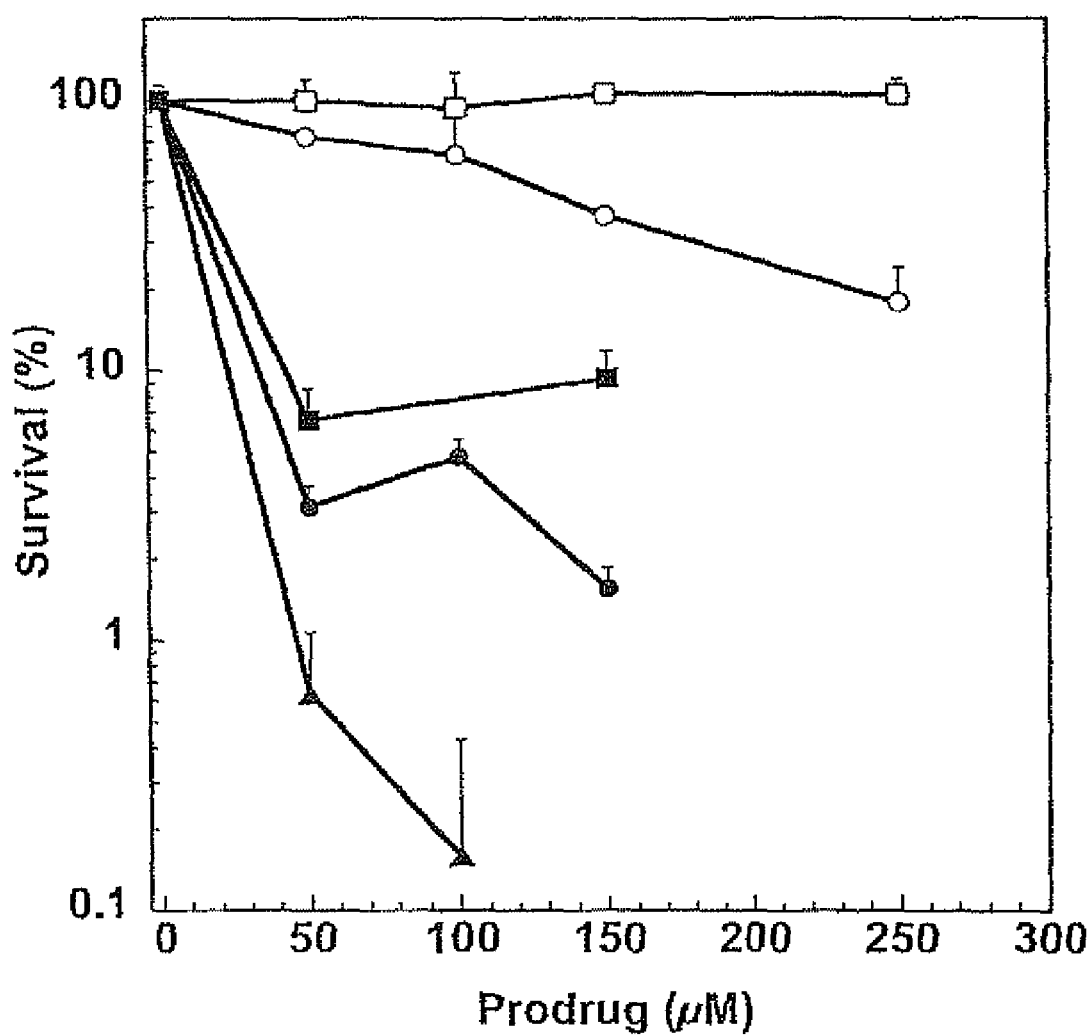
FIG. 3 depicts the % survival of HT29 cells as a function of the concentration of prodrug in a two-hour exposure to BCNU (40 μM) after prodrug pretreatment. Prodrug 2 (open squares) and prodrug 1 (open circles) were incubated for 5 hr in cell medium containing no β-glucuronidase; and prodrug 2 was incubated for 14 hr in cell culture containing bovine liver β-glucuronidase at 20 units/mL of medium (closed squares); prodrug 1 was incubated in cell culture containing bovine liver β-glucuronidase at 20 units/mL of medium for 7 hr (closed circles) or 14 hr (closed triangles).
Figure 4:
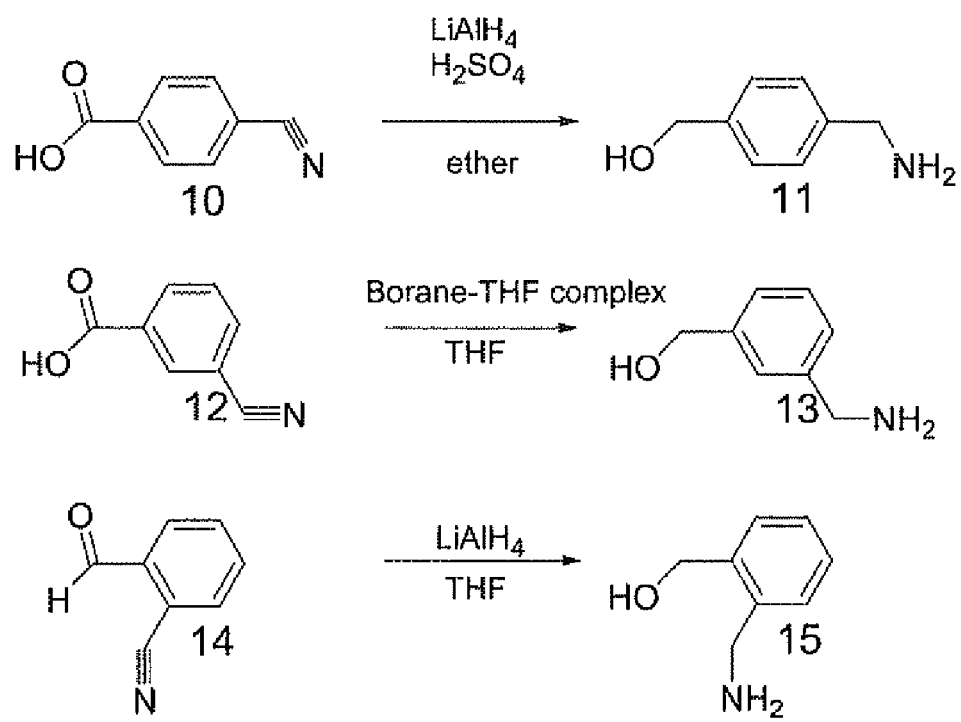
FIG. 4 depicts a reaction scheme to prepare intermediates 11, 13, and 15 for preparing compounds 24-27 in accordance with an embodiment of the invention.
Figure 5:
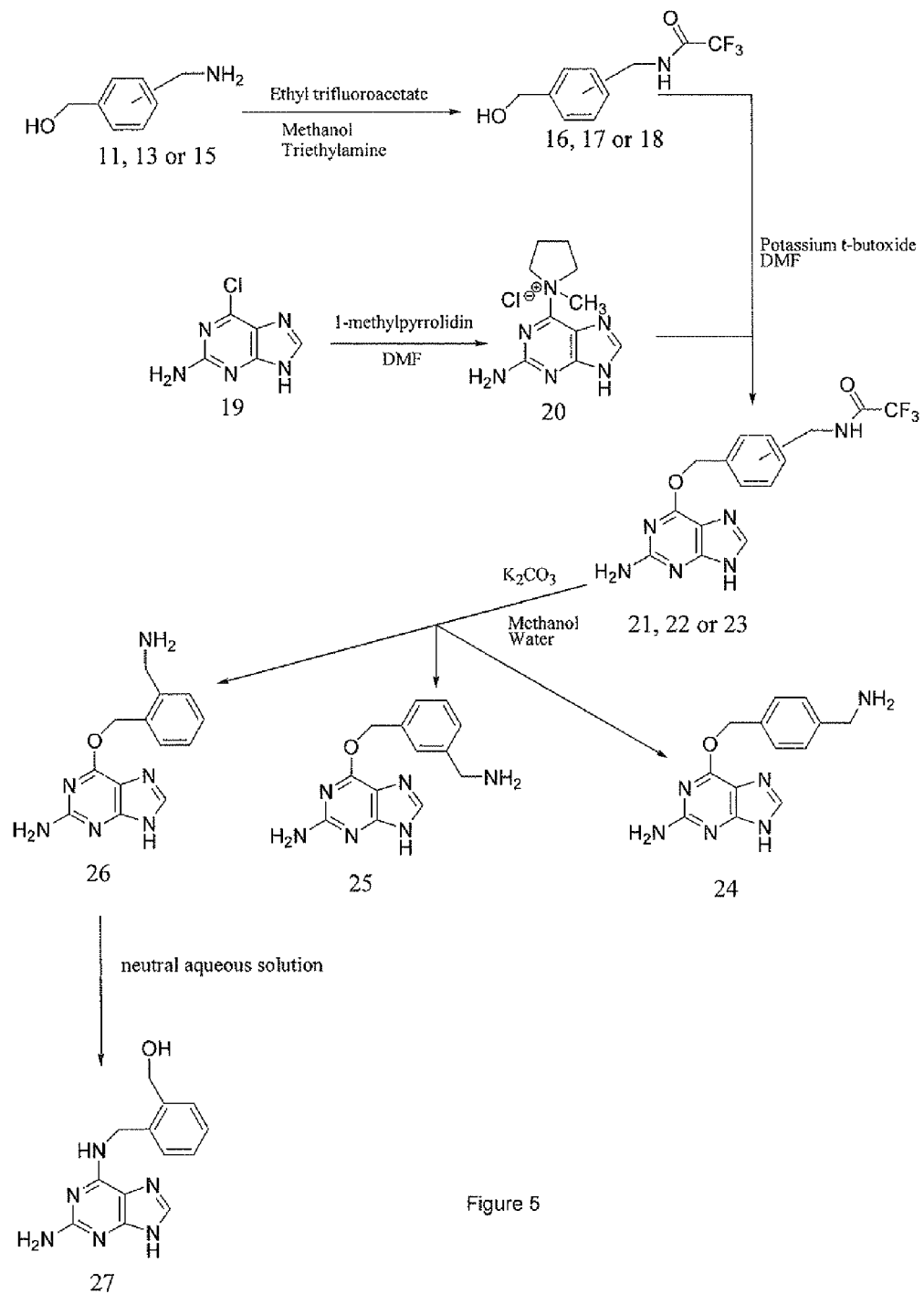
FIG. 5 depicts a reaction scheme to prepare compounds 24-27 in accordance with an embodiment of the invention.

HT29 cell killing by BCNU in combination with the prodrugs 1 and 2 is illustrated in FIG. 3. Cells treated for 5 hr with increasing concentrations of prodrugs 1 and 2 were quite resistant to killing after a two-hour exposure to 40 μM BCNU. However, when cultures containing 1 were treated with bovine liver β-glucuronidase at 20 units/mL of medium for either 7 or 14 hr, the cells were greatly sensitized to killing by BCNU. Similarly, incubation of 2 in cell cultures containing β-glucuronidase at 20 units/mL for 14 hr also led to much greater cell killing by BCNU. These results were again a consequence of liberation of $O^6$-benzylguanine from 1 or $O^6$-benzyl-2'-deoxyguanosine from 2, respectively.

These data suggest that if levels of β-glucuronidase secreted by necrotic human tumor cells are sufficiently high, the prodrugs 1 and 2 will be useful for selectively delivering $O^6$-benzylguanine and $O^6$-benzyl-2'-deoxyguanosine to tumor cells compared to normal cells. This would greatly improve chemotherapy for human tumors with the combination of alkyltransferase inactivators and either chloroethylating or methylating drugs since possible side effects associated with widespread systemic alkyltransferase inactivation would be significantly reduced.

Example 4

4-(Aminomethyl)benzyl alcohol (11): Adapting the procedure described by Keppler et al., *Nature Biotechnology* 21, 86-89 (2003), 1.5 L of 0.5 M LiAlH$_4$ were chilled on ice and 22 mL of concentrated H$_2$SO$_4$ were added dropwise. 4-Cyanobenzoic acid (10) 20 g (136 mmol) was suspended in 120 mL of ether and this was added dropwise to the sulfuric acid. The reaction was heated to reflux for 4 hours. The reaction was quenched on ice with 215 mL of water followed by the addition of 80 g of NaOH in 650 mL of water. The ether was decanted off the resulting gel and the gel was extracted twice with 600 mL portions of ether. The combined ether fractions were dried over MgSO$_4$ and evaporated under vacuum to give 13.1 g (96 mmol) of 4-(aminomethyl)benzyl alcohol (11) as a clear oil. $^1$H NMR (CDCL$_3$/TMS) δ=1.95 (broad s, 3H, —OH and —NH$_2$, exchangeable with D$_2$O), 3.86 (s, 2H, —CH$_2$—NH$_2$), 4.68 (s, 2H, —CH$_2$—OH), 7.30 (m, 4H, aromatic).

3-(Aminomethyl)benzyl alcohol (13): A 20 g sample of 3-cyanobenzoic acid (12) (136 mmol) was suspended in 100 mL of dry tetrahydrofuran (THF). Borane-tetrahydrofuran complex (400 mL of 1.0 M solution in THF) was added dropwise over one hour and then stirred for an additional 3 hours. The reaction was quenched with 220 mL of concentrated HCl:water (1:1) to cleave the borane-alcohol complex. The THF was then evaporated off under vacuum. Solid NaOH pellets, 70 g total, were added slowly to neutralize the acid and bring the pH of the solution to 12. The aqueous phase was then extracted 4 times with 500 mL portions of ether. The ether extract was dried over MgSO$_4$ and evaporated under vacuum to give 18 g (131 mmol) of 3-(aminomethyl)benzyl alcohol (13) as a light colored oil. $^1$H NMR (CDCl$_3$/TMS) δ=1.95 (broad s, 3H, —OH and —NH$_2$, exchangeable with D$_2$O), 3.86 (s, 2H, —CH$_2$—NH$_2$), 4.66 (s, 2H, —CH$_2$—OH), 7.27 (m, 4H, aromatic).

2-(Aminomethyl)benzyl alcohol (15): A 10 g sample (76 mmol) of 2-cyanobenzaldehyde (14) was dissolved in 150 mL of THF and cooled on ice. LiAlH (250 mL of 1.0 M solution in THF) was added dropwise and the reaction was allowed to warm to room temperature and stirred overnight. The following morning, 320 mL of concentrated HCl:water (1:9) was added to the reaction. The resulting emulsion was extracted 3 times with 400 mL portions of ether and then 25 g of NaOH pellets were added to the aqueous emulsion to bring the pH to 11.8. The emulsion was extracted 4 times with 300 mL portions of ethyl acetate. The combined ethyl acetate fractions were dried over MgSO$_4$ and evaporated to give 9.1 g (66 mmol) of 2-(aminomethyl)benzyl alcohol (15) as a dark oil. $^1$H NMR (CDCl$_3$/TMS) δ=3.30 (broad s, 3H, —OH and —NH$_2$, exchangeable with D$_2$O), 4.01 (s, 2H, —CH$_2$—NH$_2$), 4.65 (s, 2H, —CH$_2$—OH), 7.29 (m, 4H, aromatic).

2,2,2-Trifluoro-N-(4-hydroxymethyl)benzylacetamide (16): Under an argon atmosphere 13 g (95 mmol) of 4-(aminomethyl)benzyl alcohol (11) was dissolved in 100 mL of dry methanol and 13.4 ml (96 mmol) of triethylamine. Ethyl trifluoroacetate [15 mL (125 mmol)], was added dropwise and the reaction was stirred for 2 hours. The reaction was stopped by adding 100 mL of water and 100 ml of ethyl acetate was added. The organic layer was removed and the aqueous layer was extracted with an additional 100 mL of ethyl acetate. The combined organic layers were extracted with 100 mL of water saturated with NaCl, dried over Na$_2$SO$_4$ and evaporated to a red solid. This material was purified over a silica gel column eluted with cyclohexane:ethyl acetate (2:1) which gave 20.1 g (86 mmol) of (7) as a white solid. $^1$H NMR (CDCL$_3$/TMS) δ=1.77 (s, 1H, —OH, exchanges with D$_2$O), 4.52 (d, 2H, —CH$_2$—NH—), 4.70 (s, 2H, —CH$_2$—OH), 6.63 (broad s, 1H, —NH—CO—, exchanges with D$_2$O), 7.33 (symmetrical m, 4H, aromatic).

2,2,2-Trifluoro-N-(3-hydroxymethyl)benzyl)acetamide (17): Under an argon atmosphere 12 g (88 mmol) of 3-(aminomethyl)benzyl alcohol (13) was dissolved in 100 mL of dry methanol and 12.3 mL (88 mmol) of triethylamine. Ethyl trifluoroacetate [14.3 mL (120 mmol)] was added dropwise and the reaction was stirred for 2 hours. The reaction was stopped by adding 200 mL of water and 100 mL of ethyl acetate was added. The organic layer was removed and the aqueous layer was extracted with an additional 200 mL of ethyl acetate. The combined organic layers were extracted with 100 mL of water saturated with NaCl, dried over Na$_2$SO$_4$ and evaporated. This material was purified over a silica gel column eluted with cyclohexane:ethyl acetate (2:1) which gave 18.8 g (80.3 mmol) of (17) as a white solid. $^1$H NMR (CDCl$_3$/TMS) δ=1.84 (s, 1H, —OH, exchanges with D$_2$O), 4.52 (d, 2H, —CH$_2$—NH—), 4.70 (s, 2H, —CH$_2$—OH), 6.65 (broad s, 1H, —NH—CO—, exchanges with D$_2$O), 7.30 (m, 4H, aromatic).

2,2,2-Trifluoro-N-(2-hydroxymethyl)benzylacetamide (18): Under an argon atmosphere 9.1 g (66 mmol) of 2-(aminomethyl)benzyl alcohol (15) was dissolved in 100 mL of dry methanol and 9.2 mL (66 mmol) of triethylamine. Ethyl trifluoroacetate [10.3 mL (86 mmol)], was added dropwise and the reaction was stirred for 2 hours. The reaction was stopped by adding 100 mL of water and 100 mL of ethyl acetate was added. The organic layer was removed and the aqueous layer was extracted with an additional 100 mL of ethyl acetate. The combined organic layers were extracted with 100 mL of water saturated with NaCl, dried over Na$_2$SO$_4$ and evaporated to a red-brown oil. This material was purified over a silica gel column eluted with cyclohexane:ethyl acetate (2:1) which gave 11.55 g (50 mmol) of (18) as a brown oil, $^1$H NMR (CDCl$_3$/TMS) δ=2.20 (s, 1H, —OH, exchanges with D$_2$O), 4.61 (d, 2H, —CH$_2$—NH—), 4.78 (s, 2H, —CH$_2$—OH), 7.37 (m, 4H, aromatic), 7.76 (broad s, 1H, —NH—CO—, exchanges with D$_2$O) ppm.

1-(2-Amino-7H-purin-6-yl)-1-methyl-pyrrolidinium chloride (20): This compound was prepared from 6-Chloroguanine (19) on a 10 g scale as described by Keppler et al., (2003). The $^1$H NMR spectrum of this product was in full agreement with the data published by Keppler et al. (2003).

N-[4-(2-Amino-9H-purin-6-yloxymethyl)benzyl]-2,2,2-trifluoroacetamide (21): To a suspension of 17.3 g (74 mmol) of 2,2,2-trifluoro-N-(4-hydroxymethylbenzyl)acetamide (16) and 9.4 g (38 mmol) of 1-(2-amino-7H-purin-6-yl)-1-methyl-pyrrolidinium chloride (20) in 400 mL of dry DMF was added 16.8 g (150 mmol) of potassium t-butoxide. The reaction was stirred for 3 hours and then 6.6 mL of glacial acetic acid in 200 mL of water were added to neutralize the excess potassium t-butoxide. The reaction was evaporated under vacuum to dryness and purified on a silica gel column eluted first with methanol/dichloromethane (1/50) followed by methanol/dichloromethane (1/10). This gave 9.2 g (25 mmol) of 21 as a white powder. $^1$H NMR (DMSO-d$_6$/TMS) δ=4.40 (s, 2H, —CH$_2$—NH—), 5.47 (s, 2H, —O—CH$_2$—), 6.27 (s, 2H, guanine-NH$_2$, exchanges with D$_2$O), 7.40 (asymmetrical m, 4H, bn-Ar), 7.83 (s, 1H, guanine H8), 10.02 (broad s, 1H, —NH—CO—exchanges with D$_2$O), 12.44 (broad s, 1H, guanine H9, exchanges with D$_2$O).

N-[3-(2-Amino-9H-purin-6-yloxymethyl)benzyl]-2,2,2-trifluoroacetamide (22): To a suspension of 11.7 g (50 mmol) of 2,2,2-trifluoro-N-(3-hydroxymethylbenzyl)-acetamide (17) and 7.0 g (27.5 mmol) of 1-(2-amino-7H-purin-6-yl)-1-methyl-pyrrolidinium chloride (20) in 300 mL of dry DMF, 11.2 g (100 mmol) of potassium t-butoxide was added. The reaction was stirred for 3 hours and then 5.0 mL of glacial acetic acid in 100 mL of water were added to neutralize the excess t-butoxide. The reaction was evaporated under vacuum to dryness and purified on a silica gel column eluted first with methanol/dichloromethane (1/50) followed by methanol/dichloromethane (1/10). This gave 6.40 g (17.4 mmol) of (22) as a white powder. $^1$H NMR (DMSO-$d_6$/TMS) δ=4.42 (s, 2H, —C$\overline{H}_2$—NH—), 5.48 (s, 2H, —O—C$\overline{H}_2$—), 6.27 (s, 2H, guanine-N$\overline{H}_2$, exchanges with $D_2O$), 7.25 (m, 1, bn-Ar), 7.41 (asymmetrical m, 3H, bn-Ar), 7.83 (s, 1H, guanine H8), 10.03 (broad s, 1H, —N$\overline{H}$—CO— exchanges with $D_2O$), 12.45 (broad s, 1H, guanine H9, exchanges with $D_2O$).

N-[2-(2-Amino-9H-purin-6-yloxymethyl)benzyl]-2,2,2-trifluoroacetamide (23): To a suspension of 11.55 g (49 mmol) of 2,2,2-trifluro-N-(2-hydroxymethylbenzyl)-acetamide (18) and 9.1 g (36 mmol) of 1-(2-amino-7H-purin-6-yl)-1-methyl-pyrrolidinium chloride (20) in 300 mL of dry DMF, 11.2 g (100 mmol) of potassium t-butoxide was added. The reaction was stirred for 5 hours and then 5.0 mL of glacial acetic acid in 100 mL of water were added to neutralize the excess t-butoxide. The reaction was evaporated under vacuum to dryness and purified on a silica gel column eluted first with methanol/dichloromethane (1/50) followed by methanol/dichloromethane (1/10). This gave 4.52 g (12.3 mmol) of (23) as a white powder. $^1$H NMR (DMSO-$d_6$/TMS) δ=4.58 (d, 2H, —C$\overline{H}_2$—NH—), 5.57 (s, 2H, —O—C$\overline{H}_2$—), 6.29 (s, 2H, guanine-N$\overline{H}_2$, exchanges with $D_2O$), 7.34 (m, 3, bn-Ar), 7.53 (m, 1H, bn-Ar), 7.81 (s, 1H, guanine H8), 10.00 (broad t, 1H, —N$\overline{H}$—CO— exchanges with $D_2O$), 12.43 (broad s, 1H, guanine H9, exchanges with $D_2O$).

$O^6$-(4-Aminomethylbenzyl)guanine (24): A 2.0 g (5.5 mmol) sample of N-[4-(2-amino-9H-purin-6-yloxymethyl)benzyl]-2,2,2-trifluoroacetamide (21) was dissolved in 200 mL of methanol together with 15 mL of water containing 4 g (29 mmol) of $K_2CO_3$ and this was heated to reflux for 2 hours. The solvents were evaporated under vacuum and the sample was loaded onto a silica gel column which was eluted with dichloromethane/methanol/triethylamine (4/1/0.25). This gave 1.13 g (4.2 mmol) of $O^6$-(4-aminomethylbenzyl)guanine (24) as a white solid. $^1$H NMR (DMSO-$d_6$/TMS) δ=3.72 (s, 2H, —C$\overline{H}_2$—NH$_2$), 5.45 (s, 2H, —O—C$\overline{H}_2$—) 6.26 (s, 2H, guanine-N$\overline{H}_2$, exchanges with $D_2O$), 7.39 (symmetrical m, 4H, bn-Ar), 7.82 (s, 1H, guanine H8). Neither the guanine 9-proton nor the amino alkyl protons were observed, which may indicate a zwitterionic structure for 24.

A sample of this material was recrystalized from water for elemental analysis. Analysis calculated for $C_{13}H_{14}N_6O_1$ containing 0.2 equivalents of water: C, 57.01; H, 5.30; N, 30.68. Found: C, 57.29; H, 5.26; N, 30.52. The material was converted to the hydrochloride salt by suspending it in water and adding one equivalent of HCl. The material was then filtered and lyophilized. Analysis of the hydrochloride salt calculated for $C_{13}H_{15}N_6O_1Cl_1$ as the hemihydrate: C, 49.45; H, 5.11; N, 26,62; Cl, 11.23. Found: C, 49.61; H, 5.12; N, 26.36; Cl, 11.16.

$O^6$-(3-Aminomethylbenzyl)guanine (25): A 6.0 g (16.4 mmol) sample of N-[3-(2-amino-9H-purin-6-yloxymethyl)benzyl]-2,2,2-trifluoroacetamide (22) was dissolved in 500 mL of methanol together with 50 mL of water containing 13 g (94 mmol) of $K_2CO_3$ and this was heated to reflux for 3 hours. The solvents were evaporated under vacuum and the sample was loaded onto a silica gel column which was eluted with dichloromethane/methanol/triethylamine (4/1/0.25). This gave 3.0 g (11.1 mmol) of $O^6$-(3-aminomethylbenzyl)guanine (25) as a white solid. $^1$H NMR (DMSO-$d_6$/TMS) δ=4.02 (s, 2H, —C$\overline{H}_2$—NH$_2$), 5.48 (s, 2H, —O—C$\overline{H}_2$—) 6.30 (s, 2H, guanine-N$\overline{H}_2$, exchanges with $D_2O$), 7.48 (m, 3H, bn-Ar), 7.65 (s, 1H, bn-Ar), 7.83 (s, 1H, guanine H8). As with compound (24), neither the guanine 9-proton nor the aminoalkyl protons were observed. A sample of this material was recrystalized from water for elemental analysis. Analysis calculated for $C_{13}C_{14}N_6O_1$: C, 57.77; H, 5.22; N, 31.09. Found: C, 57.60; H, 5.26; N, 30.88. The material was converted to the hydrochloride salt by suspending it in water and adding one equivalent of HCl. The material was then filtered and lyophilized.

$O^6$-(2-Aminomethylbenzyl)guanine (26): A 2.5 g (6.8 mmol) sample of N-[2-(2-amino-9H-purin-6-yloxymethyl)benzyl]-2,2,2-trifluoroacetamide (23) was dissolved in 250 mL of methanol together with 15 mL of water containing 5 g (36 mmol) of $K_2CO_3$ and this was heated to reflux for 2 hours, The solvents were evaporated under vacuum and the sample was loaded onto a silica gel column and eluted with dichloromethane/methanol/triethylamine (4/1/0.25). This gave 1.35 g (5.0 mmol) of $O^6$-(2-aminomethylbenzyl)guanine (26) as a white solid. $^1$H NMR (DMSO-$d_6$/TMS) δ=3.82 (s, 2H, —C$\overline{H}_2$—NH$_2$), 5.55 (s, 2H, —O—C$\overline{H}_2$—) 6.27 (s, 2H, guanine-N$\overline{H}_2$, exchanges with $D_2O$), 7.24 (m, 1H, bn-Ar), 7.34 (m, 1H, bn-Ar), 7.47 (m, 2H, bn-Ar), 7.83 (s, 1H, guanine H8) ppm. As with compounds 15 and 16, neither the guanine 9-proton nor the aminoalkyl protons were observed.

$N^6$-[(2-Hydroxymethyl)benzyl]-2-aminoadenine (27): Upon attempting to recrystalize $O^6$-(2-aminomethylbenzyl)guanine (26) from water, it was observed that a solid material precipitated out of solution on heating. $^1$H NMR spectroscopy of the recovered material indicated decomposition or rearrangement. Therefore, a larger amount of this precipitate for characterization purposes was obtained by dissolving a sample of $O^6$-(2-aminomethybenzyl)guanine (26) in buffered neutral aqueous solution which was heated to 65° C. for one week. The insoluble precipitate that formed was filtered, washed with water and dried under vacuum. This material was identified as $N^6$-[(2-hydroxymethyl)benzyl]-2-aminoadenine (27). $^1$H NMR (DMSO-$d_6$/TMS) δ=4.64 (singlet, 4H, —C$\overline{H}_2$—NH and —C$\overline{H}_2$—OH), 5.30 (s, 1H, —CH$_2$—O$\overline{H}$ exchanges with $D_2O$) 5.67 (s, 2H, guanine-N$\overline{H}_2$, exchanges with $D_2O$), 7.19 (m, 2H, bn-Ar), 7.35 (m, 2H, bn-Ar), 7.47 (broad d, 1H, benzylic N$\overline{H}$, exchanges with $D_2O$) 7.65 (s, 1H, guanine H8), 12.06 (broad s, 1H, guanine H9, exchanges with $D_2O$) ppm. UV spectroscopic determination of the kinetics of conversion of 26 to 27 in buffered neutral aqueous solution at pH 7.4 and 37° C. indicated a half-life of 51 hours for the rearrangement.

Example 5

This Example provides solubility and biological activity of the $O^6$-[(4-aminomethyl)benzyl]guanine hydrochloride and $O^6$-[(3-aminomethyl)benzyl]guanine hydrochloride are set forth below, along with that of $O^6$-benzylguanine.

TABLE 3

Properties of aminomethyl benzylguanine compounds

| Compound | Solubility in water, mg/mL | $ED_{50}$ (μM) for AGT inactivation in vitro | $ED_{90}$ (μM) for HT29 cell killing by 40 μM BCNU following a 2-hr incubation with drug |
|---|---|---|---|
| $O^6$-[(4-aminomethyl)benzyl]guanine hydrochloride (24) | >100 | 0.22 | >>5 |
| $O^6$-[(3-aminomethyl)benzyl]guanine hydrochloride (25) | >100 | 0.014 | 1.75 |
| $O^6$-benzylguanine | 0.1 | 0.30 | 0.75 |

The foregoing shows that $O^6$-[(3-aminomethyl)benzyl]guanine is particularly attractive because it is very potent as an AGT inactivator and is quite water soluble, that is 20× more active than $O^6$-benzylguanine and at least 700× more water soluble than $O^6$-benzylguanine, which indicates that the compound can be more readily formulated in water or phosphate buffered saline solutions than $O^6$-benzylguanine. In addition, the 3-aminomethyl compound is far more stable under acidic conditions than is $O^6$-benzylguanine, thereby making it a good candidate for preparing oral formulations.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of the formula (I):

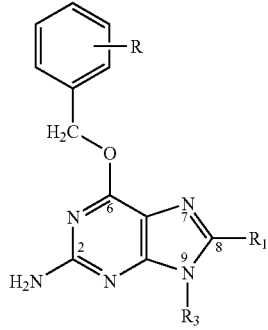

wherein R is amino $C_1$-$C_6$ alkyl;
$R_1$ is selected from the group consisting of hydrogen, halo, $C_1$-$C_4$ alkyl, $C_1$-$C_4$ hydroxyalkyl, thiol, $C_1$-$C_4$ alkylthio, trifluoromethylthio, $C_1$-$C_4$ thioacyl, hydroxy, $C_1$-$C_4$ alkoxy, trifluoromethoxy, methanesulfonyloxy, trifluoromethanesulfonyloxy, $C_1$-$C_4$ acyloxy, amino, $C_1$-$C_4$ aminoalkyl, $C_1$-$C_4$ alkylamino, $C_1$-$C_4$ dialkylamino, trifluoromethylamino, ditrifluoromethylamino, aminomethanesulfonyl, $C_1$-$C_4$ aminoacyl, aminotrifluoromethylcarbonyl, formylamino, nitro, nitroso, $C_1$-$C_4$ alkyldiazo, $C_5$-$C_6$ aryldiazo, trifluoromethyl, $C_1$-$C_4$ haloalkyl, halomethyl, $C_1$-$C_4$ cyanoalkyl, cyanomethyl, cyano, $C_1$-$C_4$ alkyloxycarbonyl, $C_1$-$C_4$ alkylcarbonyl, phenyl, phenylcarbonyl, formyl, $C_1$-$C_4$ alkoxymethyl, phenoxymethyl, $C_2$-$C_4$ vinyl, $C_2$-$C_4$ ethynyl, and $SO_nR'$ wherein n is 0, 1, 2, or 3 and R' is hydrogen, $C_1$-$C_4$ alkyl, amino, or phenyl;
and $R_3$ is selected from the group consisting of hydrogen, $C_1$-$C_4$ alkyl, $C_1$-$C_4$ aminoalkyl, $C_1$-$C_4$ hydroxyalkyl, $C_1$-$C_4$ alkylaminoalkyl, $C_1$-$C_4$ dialkylaminoalkyl, $C_1$-$C_4$ cyanoalkyl, $C_1$-$C_4$ carbamoylalkyl, $C_1$-$C_4$ pivaloylalkyl, $C_1$-$C_6$ alkylcarbonyloxy $C_1$-$C_4$ alkyl, $C_1$-$C_4$ alkoxycarbonylalkyl, ribose, 2'-deoxyribose, the conjugate acid form of a $C_1$-$C_4$ carboxyalkyl, and the carboxylate anion of a $C_1$-$C_4$ carboxyalkyl as the sodium salt;
or a pharmaceutically acceptable salt thereof;
with the proviso that when $R_1$ and $R_3$ are hydrogen, R cannot be ortho-aminoalkyl or para-aminoalkyl.

2. The compound or pharmaceutically acceptable salt of claim 1, wherein R is meta-amino $C_1$-$C_6$ alkyl.

3. The compound or pharmaceutically acceptable salt of claim 2, wherein R is meta-amino methyl and $R_1$ and $R_3$ are hydrogen.

4. A pharmaceutical composition comprising a compound or pharmaceutically acceptable salt of claim 2 and a pharmaceutically acceptable carrier.

5. A method of enhancing the chemotherapeutic treatment of tumor cells in a mammal with an antineoplastic alkylating agent that causes cytotoxic lesions at the $O^6$-position of guanine, which method comprises administering to a mammal an effective amount of the compound of formula (I) and administering to the mammal an effective amount of an antineoplastic alkylating agent which causes cytotoxic lesions at the $O^6$-position of guanine:

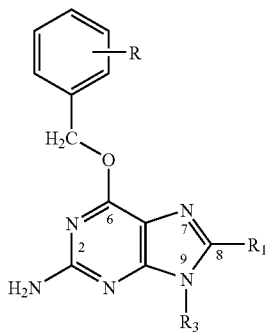

(I)

wherein R is amino $C_1$-$C_6$ alkyl;

$R_1$ is selected from the group consisting of hydrogen, halo, $C_1$-$C_4$ alkyl, $C_1$-$C_4$ hydroxyalkyl, thiol, $C_1$-$C_4$ alkylthio, trifluoromethylthio, $C_1$-$C_4$ thioacyl, hydroxy, $C_1$-$C_4$ alkoxy, trifluoromethoxy, methanesulfonyloxy, trifluoromethanesulfonyloxy, $C_1$-$C_4$ acyloxy, amino, $C_1$-$C_4$ aminoalkyl, $C_1$-$C_4$ alkylamino, $C_1$-$C_4$ dialkylamino, trifluoromethylamino, ditrifluoromethylamino, aminomethanesulfonyl, $C_1$-$C_4$ aminoacyl, aminotrifluoromethylcarbonyl, formylamino, nitro, nitroso, $C_1$-$C_4$ alkyldiazo, $C_5$-$C_6$ aryldiazo, trifluoromethyl, $C_1$-$C_4$ haloalkyl, halomethyl, $C_1$-$C_4$ cyanoalkyl, cyanomethyl, cyano, $C_1$-$C_4$ alkyloxycarbonyl, $C_1$-$C_4$ alkylcarbonyl, phenyl, phenylcarbonyl, formyl, $C_1$-$C_4$ alkoxymethyl, phenoxymethyl, $C_2$-$C_4$ vinyl, $C_2$-$C_4$ ethynyl, and $SO_nR'$ wherein n is 0, 1, 2, or 3 and R' is hydrogen, $C_1$-$C_4$ alkyl, amino, or phenyl;

and $R_3$ is selected from the group consisting of hydrogen, $C_1$-$C_4$ alkyl, $C_1$-$C_4$ aminoalkyl, $C_1$-$C_4$ hydroxyalkyl, $C_1$-$C_4$ alkylaminoalkyl, $C_1$-$C_4$ dialkylaminoalkyl, $C_1$-$C_4$ cyanoalkyl, $C_1$-$C_4$ carbamoylalkyl, $C_1$-$C_4$ pivaloylalkyl, $C_1$-$C_6$ alkylcarbonyloxy $C_1$-$C_4$ alkyl, $C_1$-$C_4$ alkoxycarbonylalkyl, ribose, 2'-deoxyribose, the conjugate acid form of a $C_1$-$C_4$ carboxyalkyl, and the carboxylate anion of a $C_1$-$C_4$ carboxyalkyl as the sodium salt;

or a pharmaceutically acceptable salt thereof;

with the proviso that when $R_1$ and $R_3$ are hydrogen, R cannot be ortho-aminoalkyl or para-aminoalkyl.

6. A pharmaceutical composition comprising a compound or pharmaceutically acceptable salt of claim 3 and a pharmaceutically acceptable carrier.

\* \* \* \* \*